(12) United States Patent
Giasolli et al.

(10) Patent No.: US 10,463,842 B2
(45) Date of Patent: Nov. 5, 2019

(54) CAGE FOR MEDICAL BALLOON

(71) Applicant: Cagent Vascular, LLC, Wayne, PA (US)

(72) Inventors: Robert M. Giasolli, Orange, CA (US); Peter Schneider, Honolulu, HI (US)

(73) Assignee: Cagent Vascular, LLC, Wayne, PA (US)

( * ) Notice: Subject to any disclaimer, the term of this patent is extended or adjusted under 35 U.S.C. 154(b) by 0 days.

(21) Appl. No.: 15/316,067

(22) PCT Filed: Jun. 3, 2015

(86) PCT No.: PCT/US2015/034060
§ 371 (c)(1),
(2) Date: Dec. 2, 2016

(87) PCT Pub. No.: WO2015/187872
PCT Pub. Date: Dec. 10, 2015

(65) Prior Publication Data
US 2017/0100570 A1 Apr. 13, 2017

Related U.S. Application Data

(60) Provisional application No. 62/007,842, filed on Jun. 4, 2014.

(51) Int. Cl.
*A61M 25/10* (2013.01)
*B29C 48/09* (2019.01)
(Continued)

(52) U.S. Cl.
CPC .......... *A61M 25/104* (2013.01); *A61L 29/04* (2013.01); *A61M 25/1002* (2013.01); *A61M 25/1029* (2013.01); *A61M 25/1036* (2013.01); *B29C 48/0022* (2019.02); *B29C 48/09* (2019.02); *B29C 63/0065* (2013.01); *B29C 65/48* (2013.01); *A61M 2025/105* (2013.01); *A61M 2025/1031* (2013.01); *A61M 2025/1081* (2013.01); *A61M 2025/1086* (2013.01); *B29L 2031/7543* (2013.01)

(58) Field of Classification Search
CPC .......... A61L 29/04; A61M 2025/1031; A61M 2025/105; A61M 2025/1081; A61M 25/1029; A61M 25/1036; A61M 25/104; B29C 47/0023; B29C 47/0066; B29C 63/0065; B29C 65/48; B29L 2031/7543
See application file for complete search history.

(56) References Cited

U.S. PATENT DOCUMENTS 5,192,291 A * 3/1993 Pannek, Jr. ..... A61B 17/320725
604/22
6,626,861 B1 * 9/2003 Hart ................. A61B 17/22032
604/96.01
(Continued)

*Primary Examiner* — Imani N Hayman
(74) *Attorney, Agent, or Firm* — Knobbe, Martens, Olson & Bear LLP

(57) ABSTRACT

A cage can be positioned around a medical balloon, such as an angioplasty balloon, to assist in a medical procedure. The cage can include a plurality of strips, each extending between a set of rings including first and second rings. As the balloon expands, the first and second rings move closer together and allow the strips to expand outward. The cage may have wedge dissectors on the strips.

22 Claims, 29 Drawing Sheets

(51) Int. Cl.
    *B29C 48/00*     (2019.01)
    *A61L 29/04*     (2006.01)
    *B29C 63/00*     (2006.01)
    *B29C 65/48*     (2006.01)
    *B29L 31/00*     (2006.01)

(56) References Cited

U.S. PATENT DOCUMENTS

| | | | | |
|---|---|---|---|---|
| 2003/0153870 A1* | 8/2003 | Meyer | A61M 25/104 | 604/96.01 |
| 2003/0163148 A1* | 8/2003 | Wang | A61B 17/320725 | 606/159 |
| 2004/0158270 A1* | 8/2004 | Wyzgala | A61B 17/320725 | 606/170 |
| 2005/0021070 A1* | 1/2005 | Feld | A61B 17/320725 | 606/194 |
| 2005/0267409 A1* | 12/2005 | Shkolnik | A61M 25/1025 | 604/103.06 |

* cited by examiner

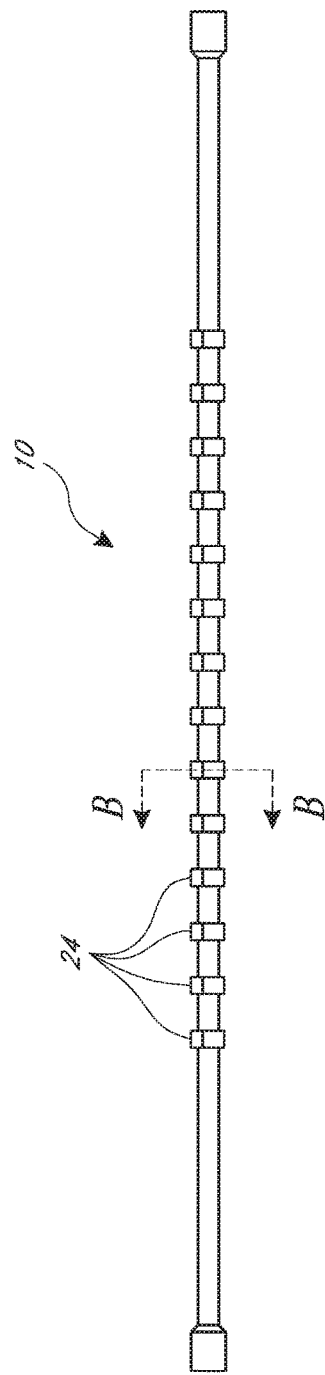

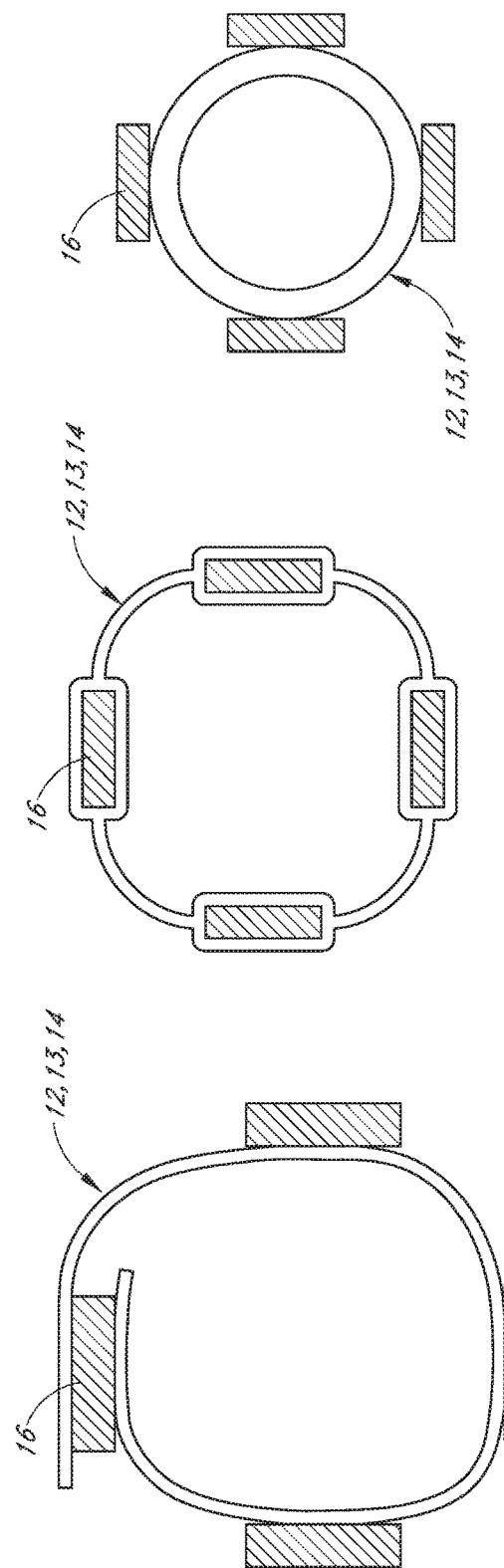

CAGE FOR MEDICAL BALLOON

CROSS-REFERENCE TO RELATED APPLICATIONS

This application is the U.S. National Phase of International Application No. PCT/US2015/034060 filed on Jun. 3, 2015, which is in turn claims the benefit of U.S. Prov. App. No. 62/007,842 filed on Jun. 4, 2014. Each of the foregoing priority applications is hereby incorporated by reference in their entireties. Any and all applications for which a foreign or domestic priority claim is identified in the Application Data Sheet as filed with the present application are hereby incorporated by reference under 37 CFR 1.57.

BACKGROUND OF THE INVENTION

Field of the Invention

Certain embodiments disclosed herein relate generally to a cage for use with a medical balloon, such as an angioplasty balloon. Methods of manufacturing the cage and treatment methods involving the cage are also disclosed.

Description of the Related Art

Atherosclerotic occlusive disease is the primary cause of stroke, heart attack, limb loss, and death in the United States and the industrialized world. Atherosclerotic plaque forms a hard layer along the wall of an artery and is comprised of calcium, cholesterol, compacted thrombus and cellular debris. As the atherosclerotic disease progresses, the blood supply intended to pass through a specific blood vessel is diminished or even prevented by the occlusive process. One of the most widely utilized methods of treating clinically significant atherosclerotic plaque is balloon angioplasty.

Balloon angioplasty is a method of opening blocked or narrowed blood vessels in the body. The balloon angioplasty catheter is placed into the artery from a remote access site that is created either percutaneously or through open exposure of the artery. The catheter is passed along the inside of the blood vessel over a wire that guides the way of the catheter. The portion of the catheter with the balloon attached is placed at the location of the atherosclerotic plaque that requires treatment. The balloon is generally inflated to a size that is consistent with the original diameter of the artery prior to developing occlusive disease.

When the balloon is inflated, the plaque is stretched, compressed, fractured, or broken, depending on its composition, location, and the amount of pressure exerted by the balloon. The plaque is heterogeneous and may be soft in some areas or hard in others causing unpredictable cleavage planes to form under standard balloon angioplasty. Balloon angioplasty can cause plaque disruption and sometimes even arterial injury at the angioplasty site.

SUMMARY OF THE INVENTION

There is a continuing need to improve the methods for treating occlusive disease, including balloon angioplasty and other related treatment systems. In some embodiments a cage can be positioned around a medical balloon, such as an angioplasty balloon, to assist in a medical procedure. The cage can include at least first and second rings and a plurality of strips. Each strip can extend longitudinally between the first and second rings. Moving the cage to an expanded position can move the first and second rings closer together while expanding the strips. In some examples, the cage may further include spikes on the strips that can be used as wedge dissectors to dissect plaque in a vessel, among other things.

The cage can be assembled and/or manufactured in many ways, including, in some examples, an extrusion process, material removal from a tube, or by splitting a wire to form the strips.

The cage can assist a medical procedure in many ways. For example, the cage may cover a drug coating on the balloon pre-deployment. In some variants, when the cage is expanded, the cage may allow access to the drug coating on the surface of the balloon. In this way, the cage can prevent or reduce the chances that the drug will become diluted during delivery or will treat areas of the body not intended for treatment.

As another example, the cage can prevent or reduce dog boning of the balloon by increasing the resistance to expansion of the combined balloon and cage at the ends of the cage as compared to the center of the cage.

In some embodiments, a balloon catheter can comprise an elongate member, a balloon, and a cage. The elongate member can have an inner lumen, the elongate member defining a longitudinal axis. The balloon can be connected to the elongate member at a distal end of the elongate member. The cage can be for positioning about the balloon. The cage can comprise a plurality of strips and a plurality of rings. The plurality of rings can be configured to secure the plurality of strips to the balloon catheter. Each strip of the plurality of strips can have a first ring of the plurality of rings at a distal end, a second ring of the plurality of rings at a proximal end. At least a portion of the strip between the distal and proximal ends remains uncovered by and/or unconnected to any ring. The balloon and cage are configured to have an initial state and an expanded state, the plurality of strips configured to move with the balloon as it moves toward the expanded state.

According to some embodiments of the balloon catheter, at least some of the rings of the plurality of rings comprise a heat shrink material. Further each strip of the plurality of strips can include a plurality of wedge dissectors spaced along a surface of the strip, each strip extending longitudinally along an outer surface of the balloon. The plurality of rings can secure the plurality of strips to distal and proximal ends of the balloon. At least some of the strips of the plurality of strips can be secured with rings at intermediate points of the balloon. The strip may be secured at intermediate points and/or at the ends.

In some embodiments, at least some of the rings of the plurality of rings comprise a part ring having a top layer of heat sink material and a bottom layer, an end of a strip of the plurality of strips sandwiched between the top layer and the bottom layer. Some embodiments can include hooks on the strips, grooves on the strips or rings, springs, and other features.

A method of retrofitting a balloon catheter with a cage can comprise any of the below steps. Positioning a plurality of strips around an inflated balloon of a balloon catheter, the strips being positioned equally spaced around the inflated balloon. Advancing rings of heat shrink material over the balloon so that each end of the strips of the plurality of strips is covered by a ring heat shrink material. Heating the rings of heat shrink material to shrink the rings of heat shrink material to thereby secure the plurality of strips to the balloon, at least a portion of each strip of the plurality of strip between distal and proximal ends of the strip remaining uncovered by and/or unconnected to any ring of heat shrink material.

A method may further include positioning positioning the strips to extend primarily longitudinally, and/or positioning the strips serially in rows around the balloon with 4 rows, each having between 2-6 strips per row. The strips can be attached either permanently or temporarily to the balloon with an adhesive.

Advancing rings of heat shrink material over the balloon further may comprise covering a distal end of distal-most strips of the plurality of strips with a single ring of heat shrink material. Further, advancing rings of heat shrink material may include covering a proximal end of proximal-most strips of the plurality of strips with a single ring of heat shrink material. Still further, it can include covering a proximal end of distal-most strips of the plurality of strips and a distal end of proximal-most strips with a single ring of heat shrink material.

In some embodiments, a cage can be positioned around an angioplasty balloon. The cage can include first and second rings and a plurality of strips. Each strip of the plurality of strips can extend longitudinally between the first and second rings. The cage can have a pre-expansion position and an expanded position, wherein moving to the expanded position moves the first and second rings closer together while expanding the strips.

A method of making a cage for an angioplasty balloon can comprise extruding a plastic tube with a plurality of spaced apart splines positioned longitudinally along the tube; cutting at least one of the splines of the plurality of splines to form a plurality of spikes positioned circumferentially around the tube; and cutting the tube to form a plurality of longitudinally extending strips, each strip including at least one spike of the plurality of spikes.

A method of making a cage for an angioplasty balloon can comprise splitting a wire into a plurality of longitudinally extending strips; cutting at least two longitudinally extending strips of the plurality of longitudinally extending strips to form a plurality of spikes spaced apart along the longitudinally extending strip; and connecting the at least two longitudinally extending strips to a first ring and a second ring such that each strip of the plurality of longitudinally extending strips extends between the first and second rings.

A method of protecting an angioplasty balloon with a drug coating can comprise providing an angioplasty balloon with a drug coating; providing a cage having a pre-expansion position and an expanded position, the cage comprising: first and second rings; and a plurality of strips, each strip of the plurality of strips extending between the first and second rings; wherein the cage is positioned over the angioplasty balloon such that in the pre-expansion position the cage covers the angioplasty balloon radially such that none, or substantially none, of the surface of the angioplasty balloon with the drug coating is exposed, and moving to the expanded position moves the first and second rings closer together while expanding the strips and exposing the angioplasty balloon surface.

A method of treating a diseased blood vessel can comprise advancing an angioplasty balloon, optionally with a drug coating, to a treatment site in a diseased blood vessel, the angioplasty balloon having a cage positioned over the angioplasty balloon, the cage having a pre-expansion position and an expanded position, the cage comprising: first and second rings; and a plurality of strips, each strip of the plurality of strips extending between the first and second rings; expanding the angioplasty balloon at the treatment site, where expanding the angioplasty balloon further comprises moving the first and second rings closer together while expanding the strips, the cage preventing or reducing dog boning of the angioplasty balloon by increasing the resistance to expansion of the combined angioplasty balloon and cage at the ends of the cage as compared to the center of the cage.

In some embodiments, a cage for positioning about an angioplasty balloon can include a plurality of rings and a plurality of strips. The plurality of rings can be non-expandable. At least one of the plurality of rings can be configured to be disposed about a first end of an angioplasty balloon, and at least one of the plurality of rings can be configured to be disposed about a second end of the angioplasty balloon. Each of the plurality of strips can include a plurality of protrusions positioned on the surface of each of the plurality of strips. Each of the plurality of rings can be configured to attach to each end of the plurality of strips. The plurality of strips can be attached to the plurality of rings through a coupling. In some embodiments, the cage can have a first length and a second length. The second length is shorter than the first length, and the plurality of rings are closer in proximity with each other such that each of the plurality of strips bends away from each of the plurality of strips.

BRIEF DESCRIPTION OF THE DRAWINGS

These and other features, aspects and advantages are described below with reference to the drawings, which are intended to illustrate but not to limit the invention. In the drawings, like reference characters denote corresponding features consistently throughout similar embodiments.

FIG. 4A shows an unfinished cage during manufacturing being cut from a tube.

FIGS. 16A-C show a plurality of embodiments of strips secured by a ring.

DETAILED DESCRIPTION OF THE PREFERRED EMBODIMENT

Figure 1A:
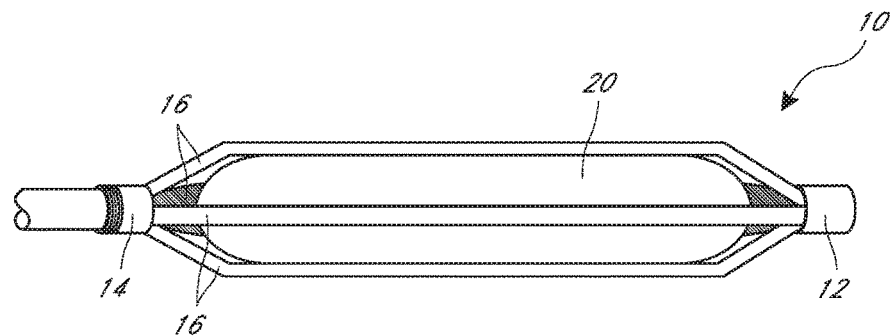
FIG. 1A illustrates a cage positioned on an angioplasty balloon in an expanded position.
Figure 1B:
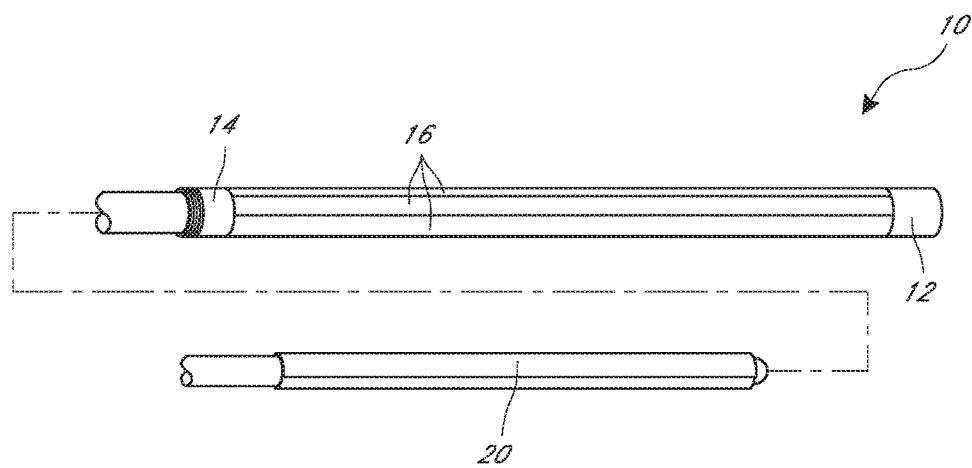
FIG. 1B shows an exploded view of an angioplasty balloon that can be positioned within a cage, both being shown in a pre-expanded position.

FIGS. 1A and 1B illustrate an embodiment of a cage 10 positioned on an angioplasty balloon 20. FIG. 1A shows an expanded position and FIG. 1B shows how the angioplasty balloon can be advanced into the cage. The cage 10 is described herein primarily with respect to an angioplasty balloon 20 and an angioplasty procedure. It is to be understood that the cage 10 can be used with other types of medical balloons and in other procedures.

The cage 10 can include a first ring 12 and second ring 14, and a plurality of strips 16. Each strip can extend longitudinally between the first ring 12 and the second ring 14. The strips and rings can be made of a monolithic part formed from a single piece of material. Thus, the first and second rings can be the ends of a cut tube, for example. The strips and rings can also be made of separate materials and be connected together. As shown the illustrated cage of FIGS. 1A and 1B has five strips 16, though other numbers of strips can be used such as 2, 3, 4, 5, 6, 7, 8, 9, 10, etc.

Figure 2:
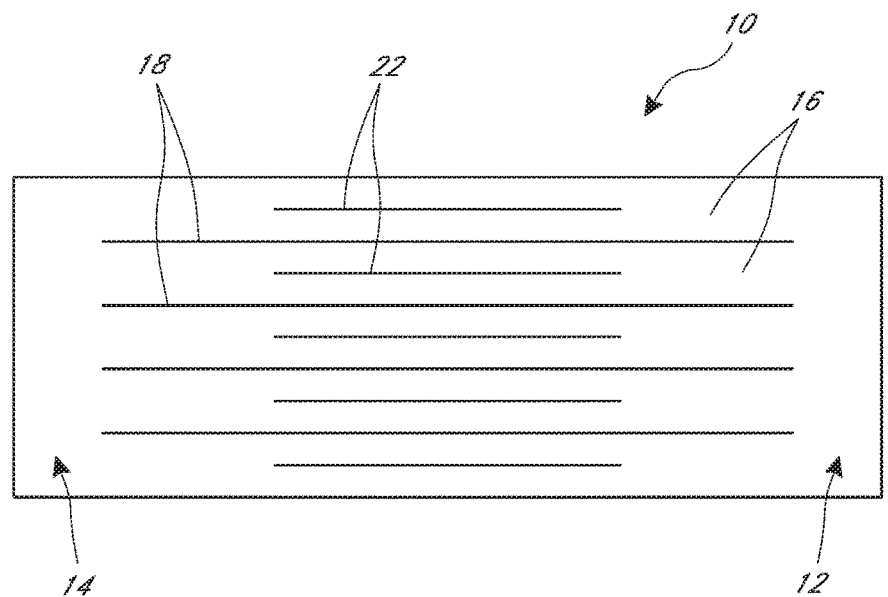
FIG. 2 shows a schematic representation of a cage laid flat showing both long and short slits.

FIG. 2 shows a plan view of a cut tube embodiment of cage, though some embodiments of cage can alternatively be made of a single flat piece of material. The material can be elastic or semi-elastic and made from a polymer, copolymer, a metal, alloy or combination of these. The strips are typically designed to enable the balloon 20 to be inflated multiple times. As well, the strips 16 can be configured such that the cage 10 can apply forces both longitudinally and axially or in orientations that enable the strips 16 to return to this original position.

In some embodiments the cage 10 is prefabricated, packaged, and sterilized separately from the balloon 20, allowing the physician to position the cage 10 around a medical balloon 20, such as an angioplasty balloon, to assist in a medical procedure at the time of the procedure. FIG. 1B shows the balloon 20 in a folded state prior to deployment and prior to placement within the cage 10. The folded balloon 20 can be advanced into the cage 10 without requiring expansion or change in shape of the cage 10. The cage 10 can completely surround and enclose the balloon 20 prior to balloon deployment or expansion. The cage 10 in the pre-expanded state can be longer than the balloon 20. This can allow for movement of one or both ends of the cage 10 towards each other while the device (e.g. balloon 20) expands. The cage 10 can be free floating over the balloon 20. One or both ends 12, 14 of the cage 10 may be fixed to the balloon 20 or another part of the delivery device. In some embodiments the cage 10 is not attached to any portion of the balloon 20 that expands. This can prevent the cage 10 from interfering with the balloon 20 as it expands.

In some examples, a cage 10 can be used with an angioplasty balloon 20 with a drug coating to can protect the drug coating. The cage 10 can prevent or reduce the premature exposure of the drug to the blood vessel. As will be understood with reference to FIG. 1B, the cage 10 can be positioned over a drug coated angioplasty balloon 20 in the pre-expansion state to prevent premature exposure of the drug to the blood vessel. The cage 10 can cover the balloon 20 radially such that a minimal amount, or substantially none, of the surface of the angioplasty balloon 20 with the drug coating is exposed. The balloon 20 and cage 10 can be advanced to a treatment location in this configuration. Though not shown, the system may be advanced over a guidewire within the vasculature.

As illustrated in FIG. 1A, the cage 10 can be moved to an expanded position. In the expanded position the first 12 and second rings 14 are closer together and the strips are expanded thereby exposing the angioplasty balloon surface. In this position, the drug can be placed into contact with diseased tissue in the blood vessel.

In currently available systems, it is generally difficult to predict how much drug will reach the diseased tissue. There are many factors that limit the ability to accurately predict how much drug will be transferred to the diseased tissue. For example, blood flow can dilute the drug on the balloon 20 as it is advanced to the treatment site. Furthermore, navigating the device through the blood vessel can cause the balloon 20 to rub against the endoluminal surface thereby removing some of the drug as the balloon 20 is being advanced to the treatment location. Therefore, in some examples, the cage 10 can offer a physical barrier to protect the drug covering of the balloon 20 during advancement to the treatment location. In this way the cage 10 can be used such that balloon 20 and drug covering are exposed to blood flow in a vessel only during expansion of the balloon 20 as the space between the strips increases. In this way, the cage 10 can prevent or reduce the chances that the drug will become diluted or that the drug will treat areas of the body that are not meant for treatment. In some variants, this can allow for more controlled delivery of the drug with a reduction in the amount of drug necessary to be coated on the balloon 20.

In some embodiments, the folded balloon 20 can be positioned entirely within the cage 10. As is illustrated in FIG. 1A, the cage 10 can have slits between each of the strips 16. In some variants, the slits can be formed by cutting between each of the strips 16 to separate them from a single piece of material. In other embodiments, the slits are really just the space between adjacent strips. The space between strips can be a minuscule amount, such as would formed by a laser cut, or much larger, such as equal to or greater than a width of the strip itself. Depending on the size of the slits, the exposed surface of the balloon 20 in the pre-expansion position is not more than 50% and can be as low as 25%, 10%, 5%, 1%, or less.

As has been described previously, expansion of the balloon 20 moves the first 12 and second rings 14 closer together while moving the strips 16 further apart radially. With the strips 16 in an expanded position, the balloon 20 is more exposed to and can interact with the vessel wall. In the expanded position, the balloon 20 can deliver a drug, stem cells, or other treatment to the vessel wall or to a diseased area of the vessel wall. When the balloon 20 is fully expanded, the exposed surface of the balloon 20 not covered by the strips 16 can be between 65% and 99%, 75% and 99%, more commonly 80% and 99%, or most commonly 90% and 99%, among other ranges.

Drug delivery using the cage 10 can be employed before, during, or after an angioplasty procedure. At the same time, it is not required that the cage cover the entire balloon, or be used to control or assist with drug delivery.

Figure 3:
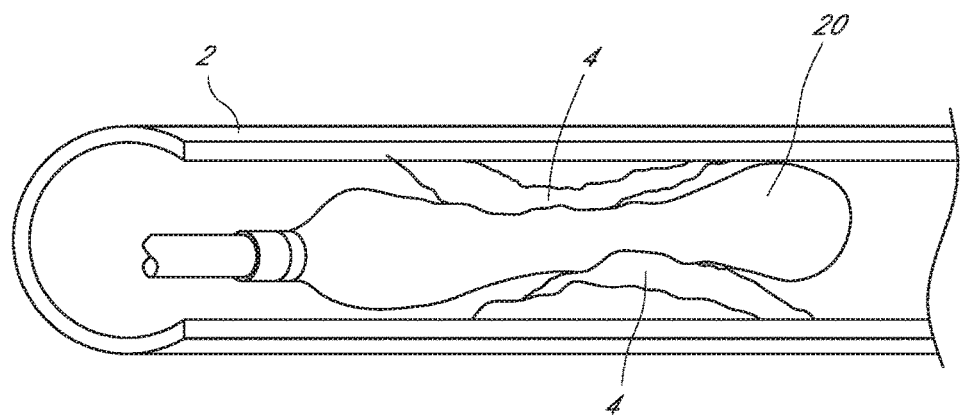
FIG. 3 shows an angioplasty balloon within a vessel at a treatment site that is experiencing dog boning.

In some embodiments, a cage 10 can be used to prevent or reduce dog boning of the balloon 20 in an angioplasty procedure. This may be in addition to, or instead of assisting with drug delivery. FIG. 3 shows an angioplasty balloon 20 within a blood vessel 2 at a treatment site. As illustrated, the angioplasty balloon 20 is experiencing dog boning as it is expanding. The plaque buildup 4 resists expansion of the balloon 20, forcing both ends of the balloon 20 to expand first, rather than focusing the expansion energy in the center of the balloon 20 at the plaque 4 where it is needed most.

To prevent dog boning, the cage 10 as shown in FIG. 1A, can constrain the balloon 20 upon expansion to encourage the middle of balloon 20 to expand first. This is because the middle area of the cage 10 can be designed to have the least resistance to expansion, being farthest away from the ends where the strips are confined by rings. This can prevent or reduce dog boning of the balloon 20 independent of the disease morphology or arterial topography the balloon 20 is expanding within.

Dog boning usually occurs where a balloon 20 expands in a vessel with plaque where the plaque resists expansion, forcing the ends of the balloon 20 to expand first (due to lack of resistance) such that the balloon 20 takes the shape of a dog bone. By enveloping a balloon 20 with a cage 10 and configuring the rings to display different expansion resistance, the ends of the balloon 20 can have the highest resistance and the center of the balloon 20 have the lowest resistance. Therefore, the cage 10 can help control and limit expansion of the balloon 20, as the balloon 20 will tend to expand more readily in the center which is typically the area of disease.

The pattern and orientation of the strips 16 can influence expansion and dog boning. Returning to FIG. 2, the short slits 22 positioned in the center of the strips 16 can reduce rigidity in the center of each of the strips 16. This can help reduce the likelihood of dog boning by further reducing resistance to expansion in the center of the cage 10.

The cage may further include spikes or wedge dissectors on the strips. The spikes can be used as a vessel preparation tool before a secondary treatment, or during a primary treatment. For example, the spikes can assist with cutting and/or perforating plaque before or during an angioplasty procedure. This may be in addition to, or instead of assisting with drug delivery and/or preventing dog boning. It will be understood that any of the embodiments described herein can provide any of these benefits and/or be used in any of these procedures, as well as the other benefits and procedures described herein.

Spikes can be positioned on the strips in any number of different orientations and configurations as will be described further below. The spikes can be any of the spikes discussed in U.S. Pat. No. 8,323,243, issued Dec. 4, 2012, entitled "DEVICE AND METHOD FOR OPENING BLOOD VESSELS BY PRE-ANGIOPLASTY SERRATION AND DILATATION OF ATHEROSCLEROTIC PLAQUE," incorporated by reference herein and included in the attached Appendix. The spikes and cage can also be used in accordance with the plaque serration methods and other methods also described therein.

Figure 4B:
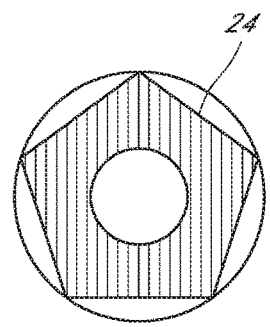
FIG. 4B is a cross-section of the unfinished cage of FIG. 4A taken along line B-B.
Figure 4C:
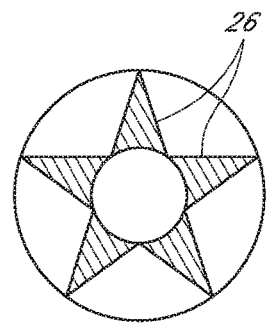
FIG. 4C shows the cross-section of FIG. 4B after an additional manufacturing step.
Figure 4D:
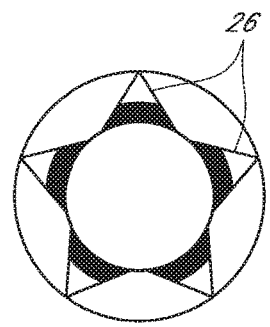
FIG. 4D illustrates a cross-section of another embodiment with a larger interior lumen.

The cage 10 can be made in many ways. For example, an extrusion process may be used, a tube may be cut, and/or a wire split as will be described in more detail below. Beginning with FIGS. 4A-5B, various embodiments of cages will be described. FIGS. 4A and 5A show embodiments of cages 10 during the manufacturing process. The cages 10 are each in the form of a tube with a plurality of splines 24 spaced apart on the tube. In some embodiments, the tube can be pre-formed and then machined to the illustrated shape. The tube can be made of metal or plastic among other materials. In other embodiments, the tube is extruded to form the illustrated shape. For example, a method of making the tube can include extruding a plastic tube with a plurality of spaced apart splines 24 positioned longitudinally along the tube. Cross-sections of the cages are shown in FIGS. 4B-D and 5A.

After forming the tube with the splines 24, material from the tube can be removed to form the slits and strips 16. Either as part of removal process, or before creating the slits, the splines may be shaped to form different shaped spikes or wedge dissectors 26. For example, the splines 24 illustrated in FIG. 4B can be machined to form the sharp wedge dissectors 26 as shown in FIGS. 4C and 4D. In some embodiments, the splines 24 can be manufactured with an additive process and shaped initially like the illustrated wedge dissectors 26 without requiring additional machining or other work.

Figure 4E:
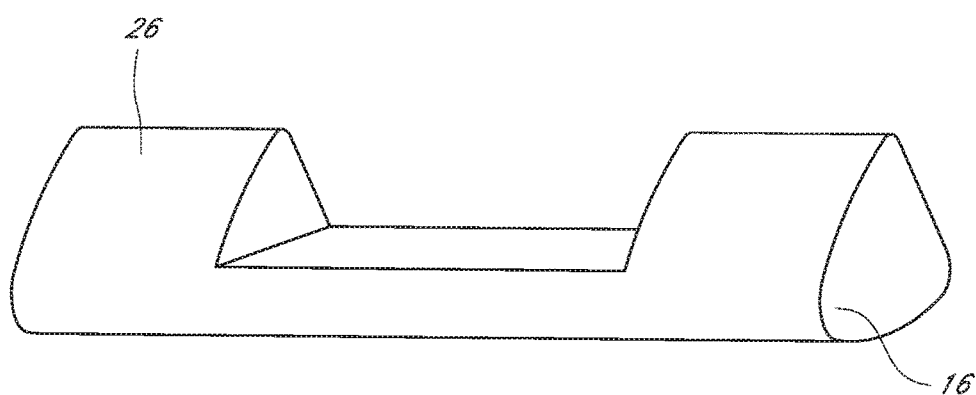
FIG. 4E shows a detail view of a portion of another embodiment of cage.
Figure 5A:
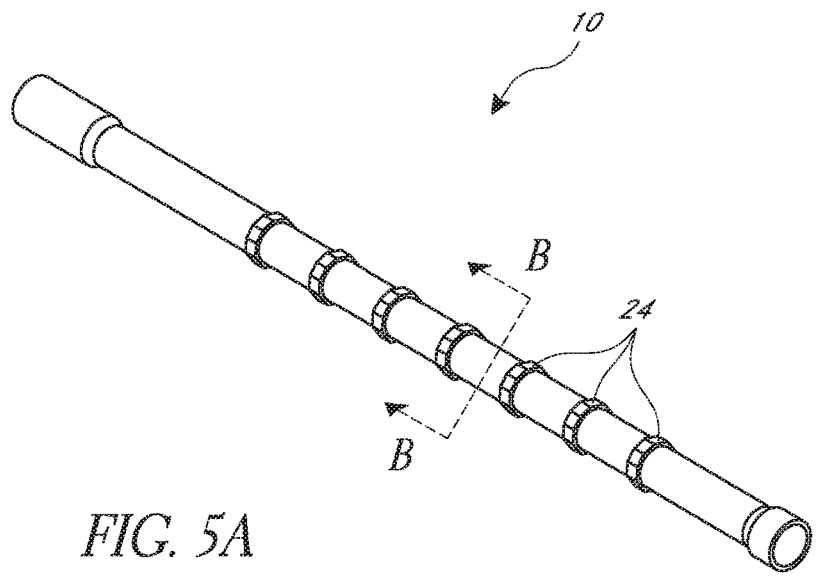
FIG. 5A shows another embodiment of an unfinished cage during manufacturing.
Figure 5B:
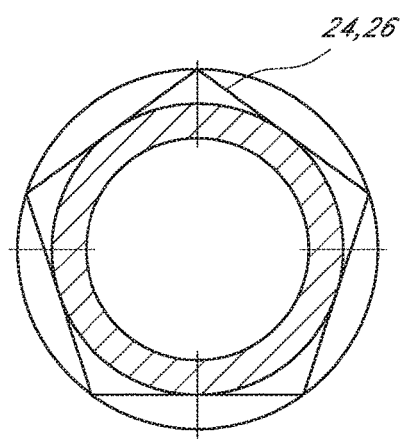
FIG. 5B shows a cross-section of the unfinished cage of FIG. 5A taken along line B-B.

Looking now to FIG. 4E, an enlarged detail view of a portion of a cage is shown. In this embodiment, the strip 16 has been formed with a plurality of spikes or wedge dissectors 26. In some embodiments, from the base of the unfinished cage of FIGS. 4A and 4B, a slit can be cut in the tube to form adjacent strips. The wedge dissectors 26 can be shaped like a tent or axe head with an elongated tip and base, both of which extend longitudinally, along the longitudinal axis of the tube. The wedge dissectors 26 can assist with cutting and/or perforating plaque before or during an angioplasty procedure. The space between the wedge dissectors 26 can be machined or otherwise formed to remove material and increase the flexibility of the strip. The space between the wedge dissectors 26 is shown as being twice the length of the wedge dissector 26, though other spacing can also be used. Typically spacing length can be 4:1 to 3:1 space to length and more commonly 3:1 to 1:1 space to length.

Turning to manufacturing of the splines, in some embodiments, the splines 26 are fabricated from a tube of material, where the cage 10 is a plastic extruded tube with splines that are cut, ground, electrical discharge machined, or molded to form the wedge dissectors 26. The tube can be manufactured with slits along its length. In some examples, the ends of the tube remain intact in order to forming rings. In some variants, the strips 16 are spaced apart with some or all the strips 16 having spikes or wedge dissectors 26. As will be understood from the above discussion, in the embodiments shown in FIGS. 4A-5B five slits would be made to form outward points.

In some embodiments, a method of making a cage 10 for an angioplasty balloon 20 can comprise first extruding a plastic tube with a plurality of spaced apart splines positioned longitudinally along the tube. In some examples, the method can then include cutting at least one of the splines of the plurality of splines to form a plurality of spikes or wedge dissectors 26 positioned circumferentially around the tube. In some variants, the method can further include cutting the tube to form a plurality of longitudinally extending strips 16, each strip including at least one spike of the plurality of wedge dissectors 26.

Figure 6A:
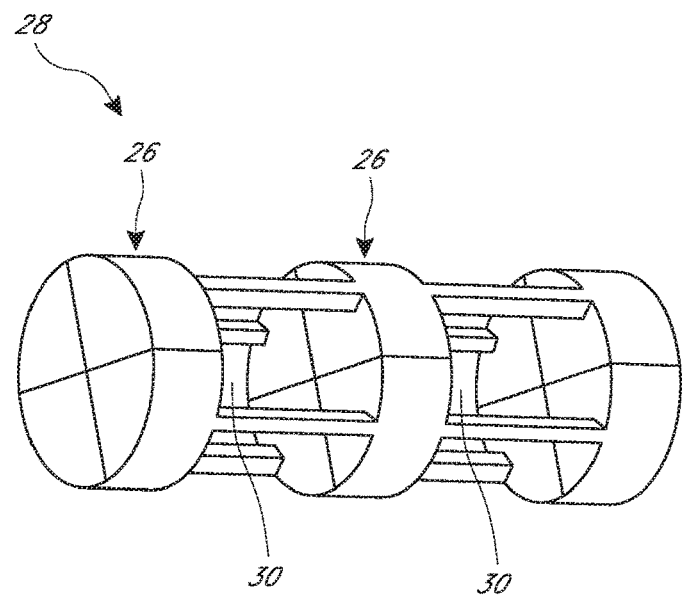
FIG. 6A shows a wire cut to form strips and wedge dissectors for an embodiment of a cage.
Figure 6B:
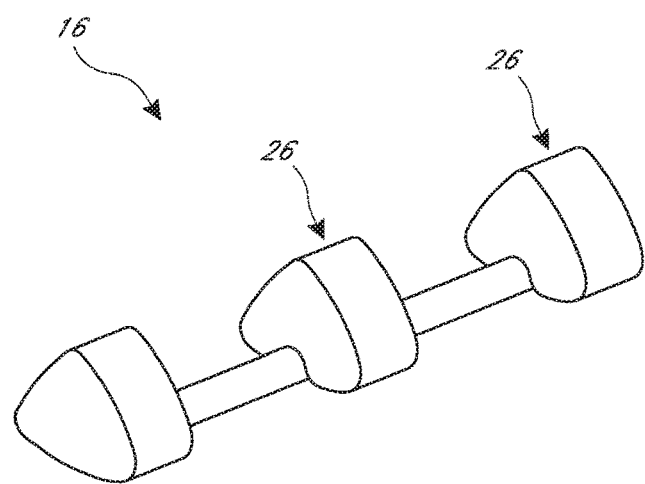
FIG. 6B shows a section of the cut wire of FIG. 6A.

Looking now to FIGS. 6A-6B, another method of manufacturing a cage 10 will be described. A wire 28 can be split or cut to form three or more strips 16 that can be used as part of forming a cage 10. In some examples, the wire 28 is constructed of an alloy, or polymeric material. Any number of different manufacturing methods can be used including laser cutting and electrical discharge machining. In some variants, the wire 28 can be divided into sections, such as four quarters. In some embodiments, square or other shaped holes 30 can be cut into the wire 28 to form spaces between the wedge dissectors 26. Each of the sections of wire can then be separated to form the strips 16 of the cage 10. A cage 10 can be assembled with a plurality of rings and include any number of strips 16. In some examples, a cage 10 can be assembled from 1, 2, 3, 4, 5, 6, 7, 8 or more strips 16.

Systems and Methods for Connecting Individual Strips

Strips 16 can be attached in many ways to form the cage 10. In addition, to forming the strips from a wire, they can also be extruded and/or formed from a flat piece of material and/or a tube. For example, it will be understood that the embodiments described with reference to FIGS. 2, 4A-5B can be modified to provide individual strips that can then be connected to form a cage.

Figure 7:
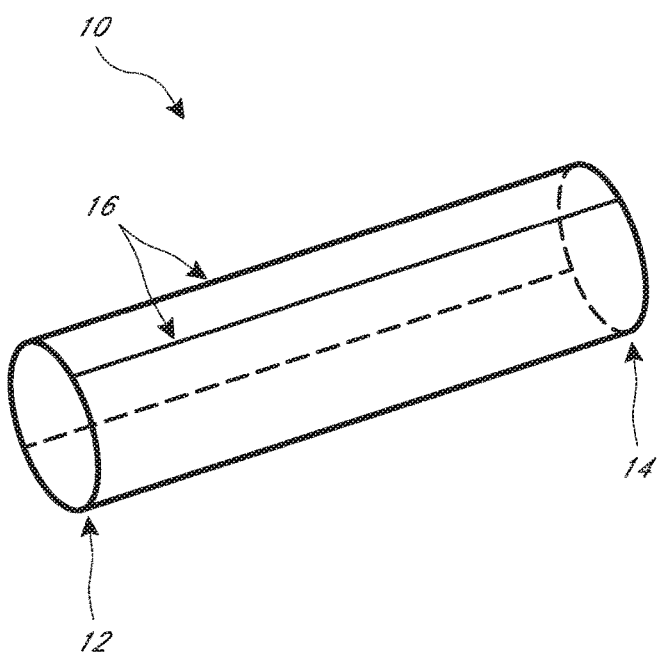
FIG. 7 shows a schematic view of a plurality of strips that are connected by two rings to form a cage.

In some embodiments, strips can be connected with two or more rings 12, 14 to form a cage 10. For instance, the individual strips of the cage 10 may be bonded to rings on either end. As illustrated in FIG. 7, each individual strip 16 is secured on either end by rings 12, 14. In constructing the cage 10, the strips 16 can be attached to the rings 12, 14 first before positioning around a balloon, or the cage can be assembled around a balloon. For example, one or more strips can be placed onto the surface of the balloon 20 before connecting to the rings. The cage 10 may be permanently fixed to one or both ends of the balloon 20 or to the balloon catheter. In some embodiments, the rings 12, 14 can hold the strips against a portion of the balloon or the balloon catheter. The strips 16 can also help to keep the balloon 20 in a compressed state prior to deployment and can assist in deflating the balloon after expansion.

The rings 12, 14 are typically circular bands, though they can be a band of any number of shapes including oval, square, elliptical, rectangular, etc. The rings can also be capable of producing a binding and/or restraining force. The rings 12, 14 can be any number of different materials including one or more of a metal, polymer, copolymer, elastomer, thermoplastic elastomer, glue, or hydrogel. The rings can be rigid or flexible.

In some examples, the rings 12, 14 can be composed of a heat shrink material or a material with elastic properties that binds, captures, or restrains the plurality of strips 16 and prevents or limits the strips 16 from moving, sliding, tilting or twisting at any point along the length of the strips but especially at either end of the balloon 20. When the rings are elastic, super elastic, or thermally active, the rings can be placed about the strips and allowed to shrink onto the strips such that the strips 16 are retained against the outer diameter of the balloon 20. Preferably, the rings and strips are positioned around a balloon in a fully expanded state and then heat is applied to the heat shrink type rings. In other embodiments, the heat shrink types rings are applied with the balloon in a deflated state.

As discussed with respect to FIGS. 1A and 1B the cage can be performed and slid onto the balloon. But, in some embodiments, assembling the cage around the balloon can allow for a smaller cage design. In retrofitting the balloon 20, the rings can be advanced onto the balloon catheter from either side which may allow for a smaller ring inner dimension as compared to a cage with one ring that is advanced over a balloon.

The rings 12, 14 of the cage 10 can be configured to accommodate the balloon 20 as it transitions from a deflated to an inflated shape. Not unlike the configuration of the cage with balloon illustrated in FIG. 1B, the strips 16 of the cage 10 can be in contact with the balloon 20 when the balloon 20 is in a deflated configuration. As the balloon 20 inflates, each strip 16 bows in a concave orientation with the balloon 20 (FIG. 1A). In some examples, the strips 16 are free-floating and not bound to the balloon surface.

As the balloon 20 begins deflating, the material properties of the strips 16 can allow it to begin to return to their original position. This may be a completely flat position. As the strips 16 return to their original position, this can provide an additional force to assist the deflation of the balloon 20. As the strips move from the concave position to a flat linear position, the strips 16 move from an expanded length ("$L_e$") to a deflated length ("$L_d$") where $L_d$ is longer than $L_e$. The straightening of the strips 16 from $L_e$ to $L_d$ in the axial direction elongates the balloon 20 and assists in more complete balloon 20 deflation.

The rings 12, 14 can come in a variety of shapes and sizes that can secure the plurality of strips 16. The following discussion of certain illustrated embodiments, are but a few such examples.

Figure 8:
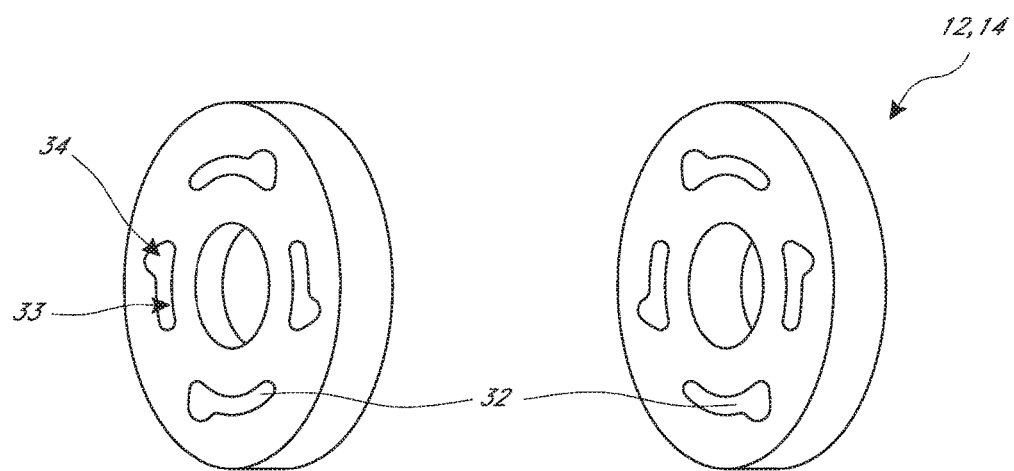
FIG. 8 illustrates a two-part ring that can be used to capture strips to form part of a cage.

The rings 12, 14 can connect to the strips 16 in a number of different ways. The rings can be mechanically attached to the strips 16 through a friction fit for example, or can be connected with an ultrasonic weld, adhesive, etc. Turning to FIG. 8, each ring 12, 14 can be a two-part ring that can connect to one or more strips 16 of the cage 10 by rotating the rings in opposite directions (e.g. clockwise and counterclockwise). The rings 12, 14 can include holes 32, through which the strips 16 can be advanced to connect to the ring. In particular, the asymmetrical shape of the holes 32 can be configured to accommodate a strip 16 with periodically spaced wedge dissectors 26 such as that illustrated in FIG. 6B.

As illustrated, the holes 32 can have a narrowed portion 33 and a wider portion 34. The wider portion 34 can be configured to accommodate the wedge dissector 26 while the narrowed portion 33 can be configured to accommodate the width of the strip 16 (i.e. the space between wedge dissectors). The strips 16 can be advanced through the holes 32 by fitting a wedge dissector 26 through the wider portion 34. In some examples, the strip 16 can then be secured by turning the rings 12, 14 such that the strip 16 is moved into the narrowed portion 33. This can secure the strips 16 to the rings 12, 14 as the wedge dissector 26 cannot move past the narrowed portion 33. As described above, both rings 12, 14 can be present at either end of the cage 10. Additionally, as illustrated in FIG. 8, because the holes 32 of the ring 12 and the holes 32 of the ring 14 are opposed, by rotating the two parts of the ring in opposite directions, this further prevents movement of the strips 16.

Figure 9A:
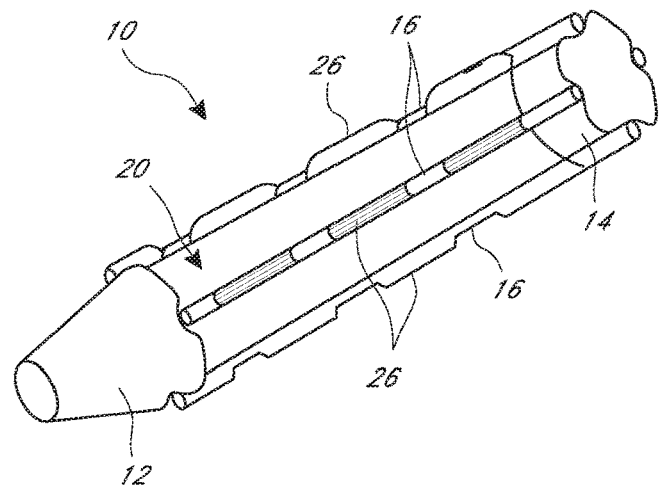
FIG. 9A is another embodiment of cage with a conical ring.

The strips 16 can be secured by rings 12, 14 that are formed from a variety of shapes. For example, FIG. 9A illustrates an embodiment of the cage 10 where the strips 16 are secured with a conical ring 12 at the distal end. The conical end can be the distal end of the balloon catheter and can provide an atraumatic end of the device.

Figure 9B:
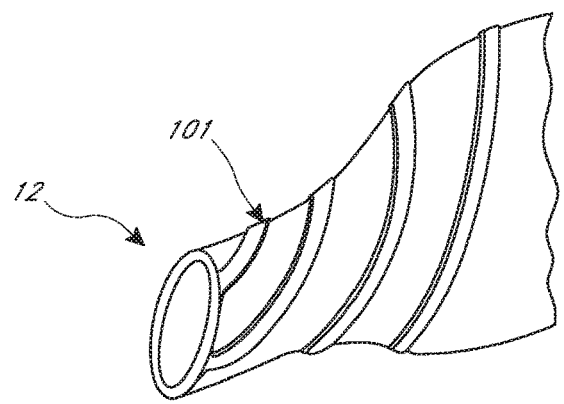
FIG. 9B is a perspective view of a ring with a tapered outer diameter wherein the ring includes a screw-like feature on its outer surface.

Similarly, FIG. 9B shows a ring 12 with a tapered outer diameter with a screw feature 101 on its outer surface. This screw feature 101 can provide either a negative or positive impression about the outer surface of the distal ring.

The ring 12 illustrated in FIG. 9B can serve a treatment purpose as well. In some examples, the tapered and screw features on the ring can assist the balloon 20 in navigating and entering a narrow lesion. The coiled outer surface 101 can be configured to provide a gripping or tunneling mechanism. This feature can allow the ring to aid the operator in navigating through occluded lesions (either totally or partially) and enable passage of the balloon 20 therein. The negative or positive impression 101 can be circumferential or patterned like a cork screw. In some embodiments, the negative or positive impression 101 can be macro in scale or have micro features that offer an enhanced surface to enable passage through a narrowing in a vessel. In some examples, the function of the outer surface 101 of the ring can be described as acting like a lubricant although the feature is mechanical in nature. This function can be further enhanced with hydrophilic, hydrophobic coating. The surface texture can also be modified to aid in passages with less penetration energy. In some embodiments, this can be accomplished by adding micro scales (as seen in porcupine quills) or enhanced surface roughness (as used in nature by mosquitos).

The ring 12 illustrated in FIG. 9B can be secured to strips 16 that are disposed about the surface of the balloon circumferentially in a helical fashion. In contrast to the linear strips 16 illustrated in FIG. 9A, the strips 16 attached to the tapered ring 12 can be wound around the balloon. A tapered or untampered ring 14 can be used at the proximal end of the balloon. In some examples, the configuration of the attached strips 16 can follow the same pattern as the negative or positive impression 101 on the ring 12.

Figure 10:
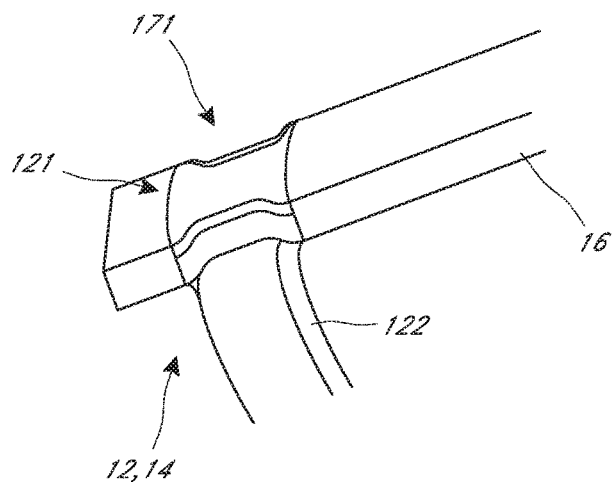
FIG. 10 shows the end of a strip configured to accommodate and be secured by a multi-layer ring to form an end of the cage.
Figure 11:
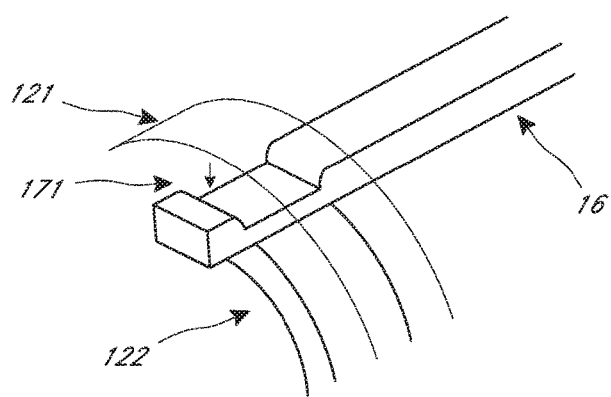
FIG. 11 illustrates another embodiment of the end of a strip configured to accommodate and be secured by a multi-layer ring to form an end of the cage.

Turning now to FIGS. 10-11, multiple layer rings will be discussed. A ring with multiple layers can be used to hold the strips between the layers. The ring can have at least a base layer 122 and a top layer 121. As seen in FIGS. 10-11, the ring 12, 14 can have a non-compressible bottom layer 122 and a compressible, thermally or electrostatically compressible layer 121. The top layer 121 can be configured of a compressible material while the base layer 122 can be configured of a non-compressible material and the strips 16 can be captured between them. In some examples, the top layer or the top and base layers can be made from a heat shrink material. In some embodiments, the ring 12, 14 can be formed from lengths of materials that are wound around themselves to form a layer of ring.

The rings can be made of a layer of composite materials where the base layer 122 is less compressible or elastic than the top layer 121. Energy can be added to the top layer 121 to produce a reduction in the top layer's diameter until the top layer compresses and captures the strips between the base layer 122. For example, the top layer 121 can be a heat shrink material. In this way, the top layer 121, base layer 122 and strips 16 can form a cage 10 as seen in FIGS. 10 and 11. In some embodiments, the strips can be attached to the balloon and/or balloon catheter with the rings that are made of a single layer of heat shrink material positioned over the strips similar to just the top layer.

The strips or rings can include indentations to facilitate attachment to the other. The strip 16 can include an indentation 171 on either side of the strip 16 (as illustrated in FIG. 10) or an indentation 171 on one surface of the strip 16 that can form a groove (as illustrated in FIG. 11). Though in FIG. 11, the top layer 121 is shown as a heat shrink material, it will be understood that in other embodiments a rigid ring could be press fit into the indentation 171. Such a rigid ring could be part of a single or multiple layer ring, thus there may or may not be a corresponding base layer 122.

Figure 12:
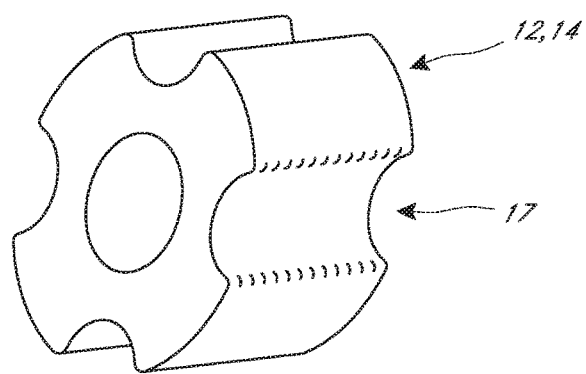
FIG. 12 is a perspective view of a ring.

FIG. 12, illustrates another embodiment of the ring 12, 14. Here, the ring 12, 14 can include a plurality of indentations or grooves 17. The grooves 17 can have a width that can accommodate the width of the distal end of strip 16. An end of a strip can be attached to the ring 12, 14 in the grooves 17 through the use of adhesive, mechanical coupling, wrapping heat shrink material around the ring, etc. In some embodiments, the strip 16 of FIG. 11 can be placed in the ring 12, 14 of FIG. 12 so that the indentations are engaged with each other.

Figure 13A:
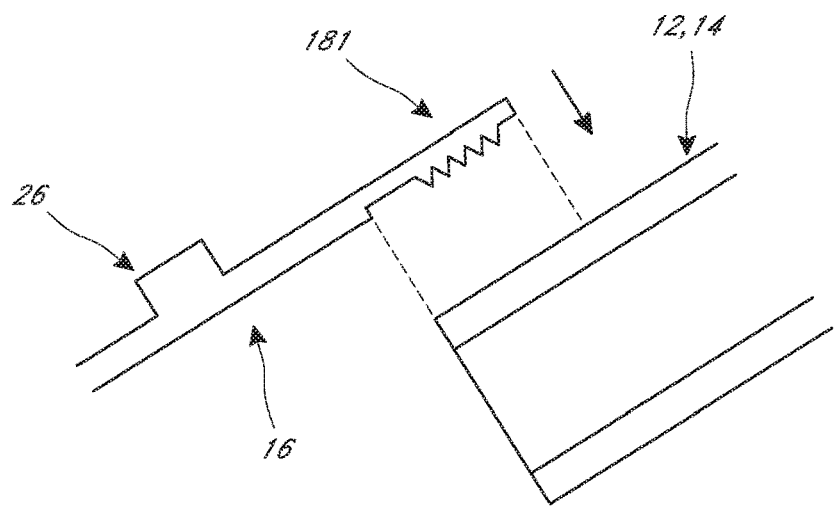
FIG. 13A shows a strip with a hook feature and ring.
Figure 13B:
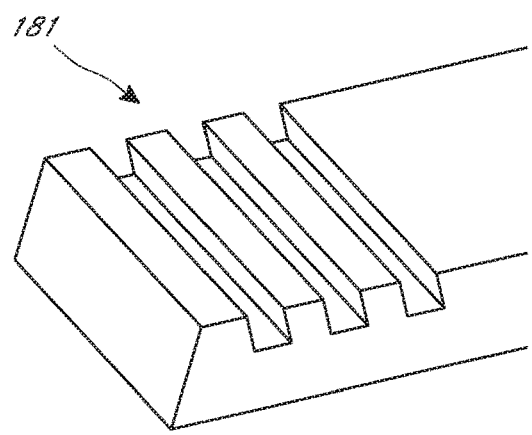
FIG. 13B is an end view of strip with a ridged hook feature.
Figure 13C:
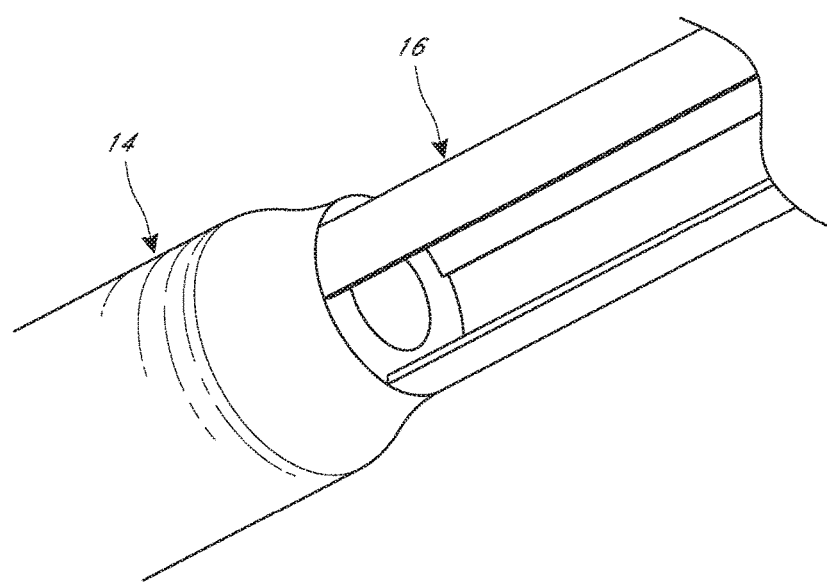
FIG. 13C shows a perspective view of a portion of a cage.

FIGS. 13A-C illustrate examples of a strip 16 that includes an securement feature 181 that improves the hold of the strips 16 to the rings 12, 14. In some variants, the securement feature 181 forms a section of the strip 16 with a higher surface roughness. This can be in the form of the illustrated ridges or other teeth-like elements that aid in the imbedding of the strip 16 into or holding the strip on the ring.

When the ring 12, 14 is a polymeric material, the securement feature 181 can be formed as narrow sections of the strip 16 at the ends (as illustrated in FIG. 13A-B), or placed strategically along the strip length (such as where three or more rings are used). The securement feature 181 can be aligned with the rings 12, 14. During fabrication, the securement feature 181 can be pressed into the polymeric material as illustrated in FIG. 13A at a high temperature where the polymeric material is near or greater than the glass transition temperature of the material. In so doing the securement feature 181 can be used to engage or connect the strips 16 to the rings 12, 14 as illustrated in FIG. 13C.

In FIG. 13A the ring 12, 14 is shown to incorporate the securement feature 181 into the body of the ring material. FIG. 13A shows the strip 16 with a ridged hook feature 181 before it is pressed into the ring material. FIG. 13B shows a perspective view of another embodiment of securement feature 181. In some examples, the securement feature 181 can be significantly longer than the ring 12, 14 is wide and be designed to provide tension on the cage 10.

When the ring 12, 14 is made from an elastic material, such as rubber or polymer, or metallic alloy or a design with elastic properties like a spring, the ring 12, 14 can be used to provide tension on the cage 10 to enable the cage 10 to return to the relaxed, deflated balloon 20 position. Furthermore, the portion of the strips 16 without a wedge dissector is the thinnest and the most flexible. This can allow the strip 16 to be the most flexible at the edge of the balloon 20 where the forces are the highest.

Figure 13D:
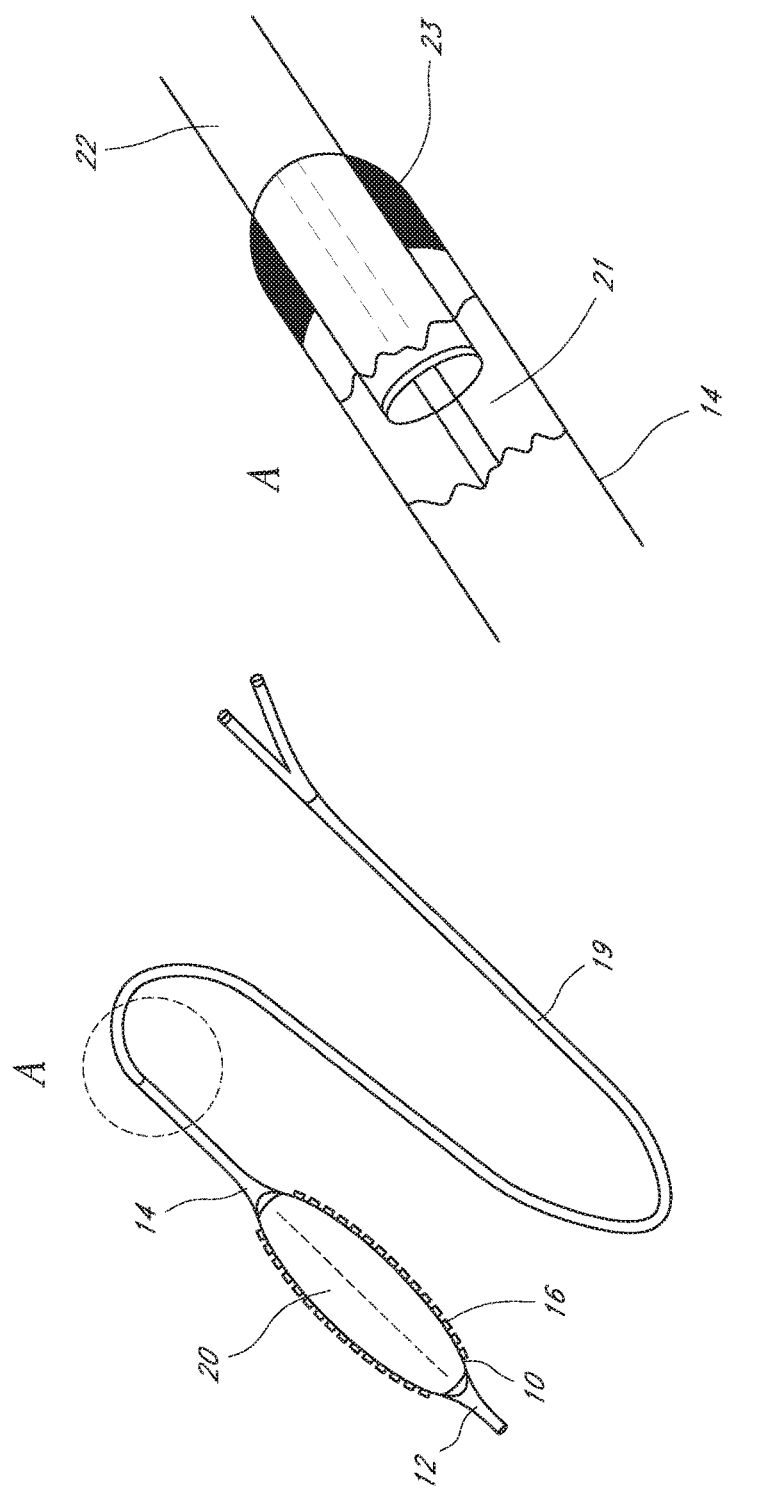
FIG. 13D illustrates a view of a conical distal ring retaining a plurality of strips.
Figure 13F:
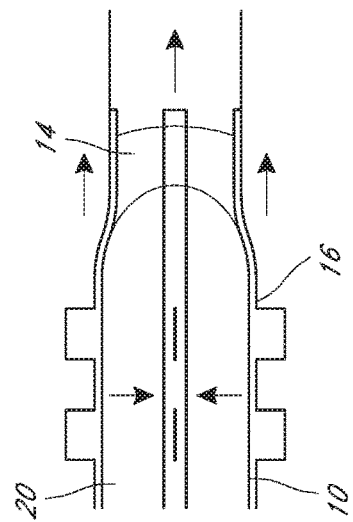
FIGS. 13E-F show a view of one end of a balloon with a cage disposed about the balloon and the forces applied to the balloon during inflation and deflation.
Figure 13E:
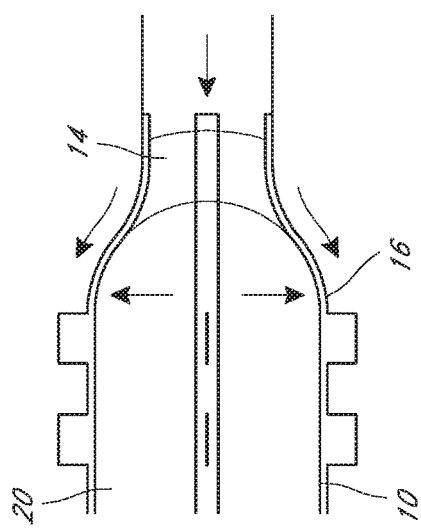

FIGS. 13D-F illustrate an example where the elastic material of a ring can provide tension on a cage during expansion and to then assist in deflating the balloon as the tension is released. Turning first to FIG. 13D, the cage 10 is disposed about the balloon 20. The cage 10 can be composed of a plurality of strips 16 that are secured to the balloon by rings 12, 14. In some examples, the rings 12, 14 can be made from long elastic material that can aid in pulling the strips 16 down into a linear position such that the wedge dissectors are perpendicular to the surface of the balloon 20. Callout "A" provides a schematic, see-through view of the proximal end of ring 14. As shown, ring 14 is secured about the outer catheter shaft 22 by an adhesive 23. As well, an inner guidewire shaft 21 can run concentric to the balloon 20. The guidewire shaft 21 can be secured with relationship to the catheter shaft 22. For example, the guidewire shaft 21 and the catheter shaft 22 can both be connected to different ports on a hub, such as the illustrated bifurcated luer at the proximal end of the balloon catheter. The balloon can be inflated by injecting a fluid into the catheter shaft. It will be understood that in some embodiments the catheter shaft 22 open directly inside the balloon 20, rather than opening at the ring 14 as shown. The ring can be attached to the catheter shaft 22 and/or the balloon 20.

FIGS. 13E-F illustrate a balloon 20 and cage 10 as the balloon 20 is inflated and subsequently deflated. As noted above, in some examples, the elastic material of the rings 12, 14 can stretch to allow the cage 10 to expand as the balloon 20 is inflated. In some embodiments such as the shown in FIGS. 13E-F, the rings can be made of an elastic polymer and the strips can be made of metal or an inelastic polymer. As shown in FIG. 13E, as the balloon 20 is inflated, the strips 16 of the cage 10 begin to move apart. In order to push each of the strips 16 outward, force is exerted radially outwards (as illustrated by the arrows) on the balloon 20—and by extension the cage 10—as the balloon 20 is inflated. As the balloon 20 expands, the rings 12, 14 are under tension and able to stretch enough to allow the strips 16 to maintain alignment while expanding with the balloon 20.

This tension can also help the balloon 20 to deflate. During balloon deflation, as illustrated in FIG. 13F, the tension on the strips 16 exerts a force radially inward as the strips 16 and the rings 12, 14 tend to want to return to a relaxed state. This force pulls on the strips 16 and allowing them to flatten, thereby providing a narrowed profile for catheter retraction.

Figure 14A:
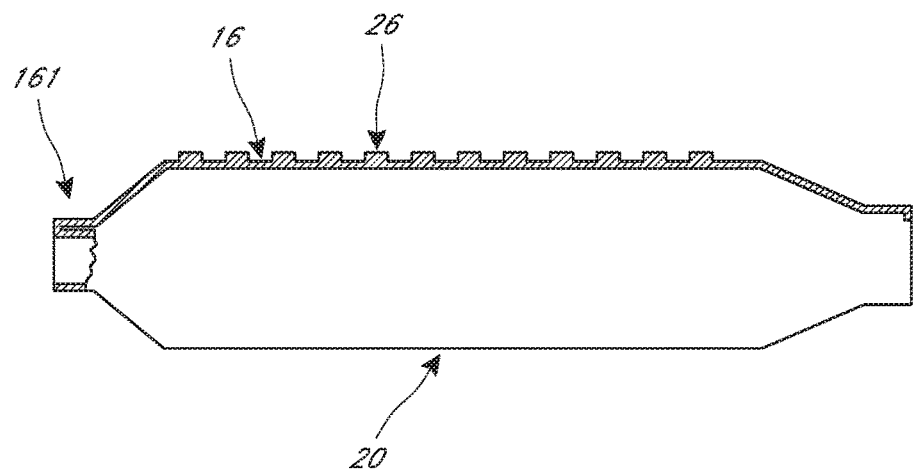
FIG. 14A illustrates a side view of an embodiment of a cage having strips with hooks that can attach to the inside of a balloon neck.
Figure 14B:
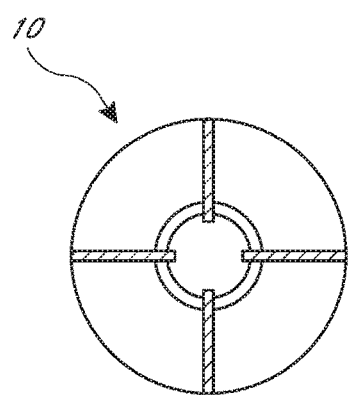
FIG. 14B shows an end view of a cage attached to a balloon as illustrated in FIG. 14A.

Looking now to FIGS. 14A-D another embodiment of strip 16 is shown with various types of rings. As illustrated in FIGS. 14A-B, in some examples, the ring can be fabricated from the lip on the neck of the balloon 20 and the portion of the catheter body used to bond the catheter to the balloon 20. The catheter can provide a pathway for gas or liquid inflation of the balloon 20. Additional components such as an over mold or heat shrink can be added to the bond joint, as can additive glue or polymeric material. In some examples, this can serve to prevent pressure from leaking out of the balloon 20 along the length of the strips 16 forming the cage 10.

As illustrated in FIGS. 14A-D, a hook 161 at the strip end can enable the strip to be easily aligned along the balloon surface and can aid in orienting the strip in a longitudinal orientation relative to the axis of the balloon 20. The hook 161 can be integrated into each end of the strip 16. The hook 161 can be wrapped around the lip of the neck of the balloon 20 from the outer diameter ("OD") of the balloon 20 neck around the opening and into the neck where the end of the hook 161 rests within the inner diameter ("ID") of the balloon 20 neck.

Both ends of the strip 16 can have a hook 161, or just one end can have the hook. In addition, the ends can be attached to the balloon catheter in the same or in different ways. For example, heat shrink can be wrapped around the ends of the strips and balloon. In some embodiment, heat shrink is wrapped around one end and a rigid ring, such as those discussed with respect to FIGS. 8-12 can be used at the other end, which may also include a heat shrink layer.

The strip may or may not be attached to the balloon at other locations. As shown, the strip 16 can also have hinges or pre-bent regions that correspond with the shape of the balloon. Thus, the strip in the expanded state can have a main portion having wedge dissectors 26 that is parallel with the axis of the balloon. Angled sections can extend from the main portion to the hooks 161. The angled sections can form an angle when the balloon is expanded as shown, but can be flat when the balloon is deflated. In some embodiments, hinges between the sections can be formed with thinner sections of material.

As shown in FIG. 14A the strip can attach to the balloon without a separate ring by use of the hooks 161. The balloon can be glued to a catheter (for example an elongated tube with one or more lumen) which can also secure the hook in place. FIG. 14A shows one strip for simplicity, though it will be understood that 2, 3, 4 (FIG. 14B), 5, or more strips could be used.

Figure 14C:
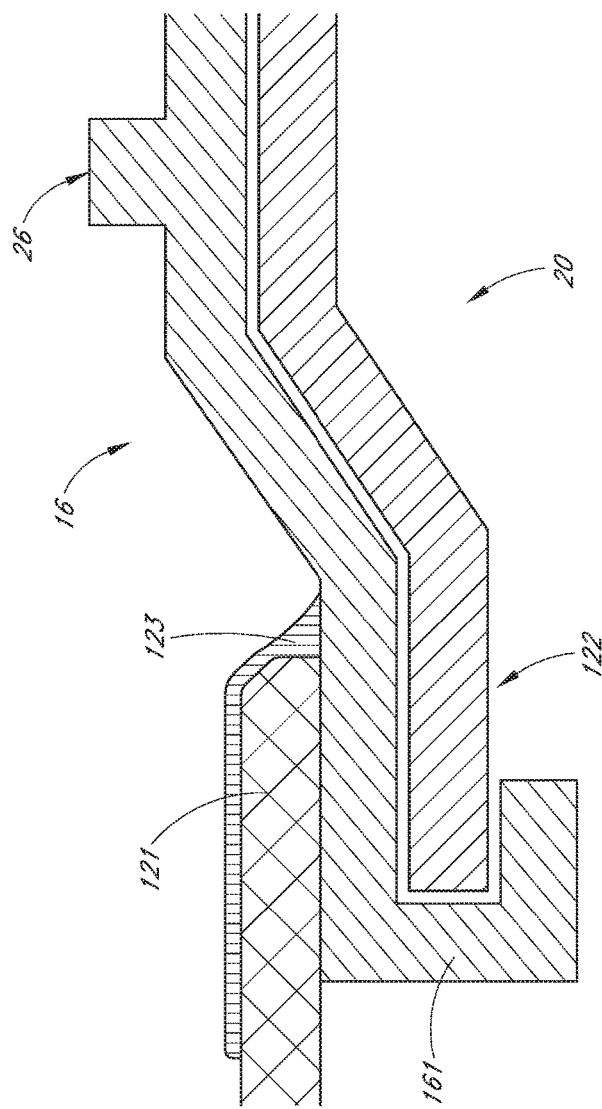
FIG. 14C is a cross sectional schematic view of the strip with hook locked into the balloon neck.

FIG. 14C shows a detail view of the hook 161 attaching to a balloon 20. As can be seen the balloon can serve as a base layer 122 of the ring and a top layer 122 is also shown. Adhesive 123 is also shown securing the top layer 121 to the balloon. In some embodiments, the top layer 121 can be the tube of the catheter.

Figure 14D:
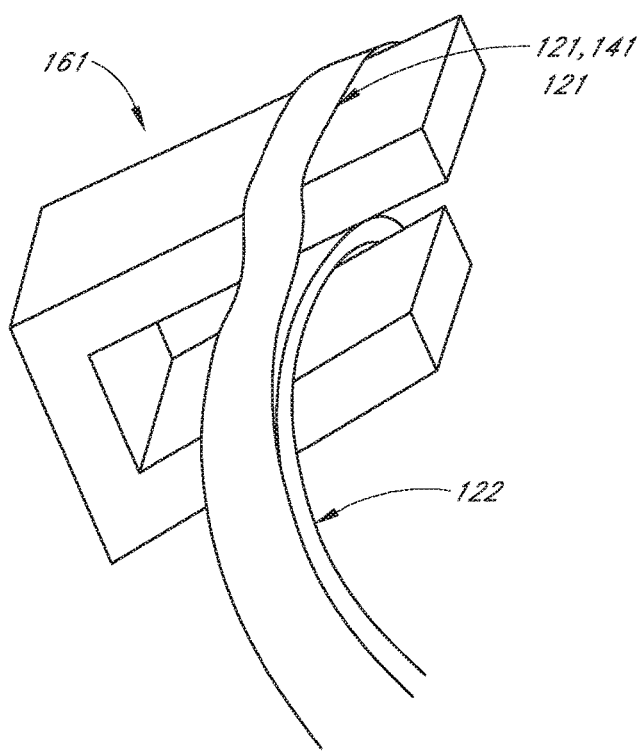
FIG. 14D is an alternative embodiment of the end of a strip with a multi-layer ring to form an end of the cage.

FIG. 14D shows a two layer 121, 122 ring. The two-layer ring can include two layers of heat shrink material. As discussed for FIGS. 10-11, the ring illustrated in FIG. 14D can be a multi-layer ring where the base layer 122 is less compressible or elastic than the top layer 121 and where energy is added to the top layer producing a reduction in the top layer's diameter until the top layer compresses and captures the strips between the base layer 122 and the top layer 121 to produce the cage 10.

Figure 14E:
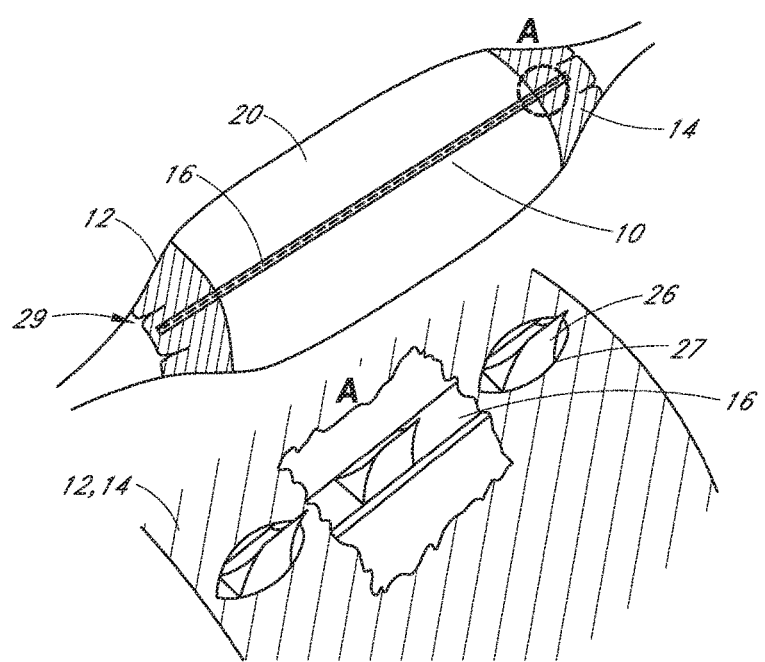
FIG. 14E shows an embodiment of a strip retained by a plurality of rings with the wedge dissectors protruding from the plurality of rings.

FIG. 14E illustrates another embodiment of the rings 12, 14 that secure the strips 16 on the surface of the balloon 20. As shown in callout "A," the rings 12, 14 can be secured to the balloon 20 such that the wedge dissectors protrude through the surface of the rings 12, 14. Callout "A" includes a cut away of the ring 12, 14 in the center in order to show the strip 16 below. The wedge dissectors can protrude through the rings 12, 14 in a variety of ways. For example, the shape of the wedge dissector can cut through the material of the rings 12, 14 as the rings 12, 14 are secured to the strips 16. This can form a hole 27. The rings 12, 14 can also have a plurality of holes 27 pre-cut into the rings 12, 14 to allow the wedge dissectors to extend through.

It can also be seen that the rings 12, 14 can be shaped to correspond with the taper of the balloon 20. For example, cutouts 29 of material in the rings can help a ring made of heat shrink material to shrink to the shape of the balloon.

As discussed above, each of the strips 16 can extend between one or two rings, though additional rings can be used as needed. For example, three, four, five, six, seven, eight, nine, or ten, or more rings can be used, especially with longer balloons. As one example, an angioplasty balloon 20 having a length of 300 mm can be fitted with a cage 10 having two rings 12 and 14 at either end. In addition to the rings 12, 14, the cage 10 can include rings 13 or other similar controlling elements that can aid the strips 16 in maintaining alignment and orientation as the balloon 20 expands towards the artery wall.

Figure 15A:
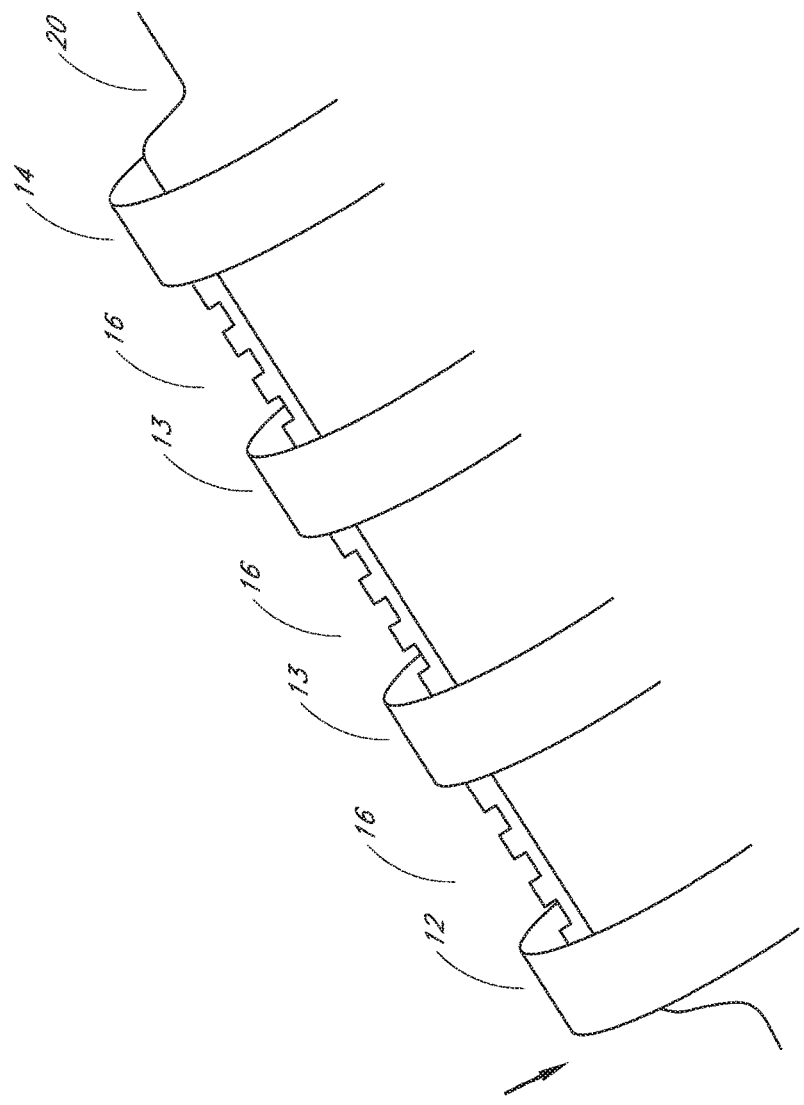
FIG. 15A illustrates a partial view of an embodiment of an angioplasty balloon with an embodiment of a strip bound to the angioplasty balloon with a plurality of ringed material to form a cage.

As illustrated in FIG. 15A, the rings 13 can be a fraction of the overall length of the balloon 20. Some ring 13 designs are less than one and a half times the length of the balloon 20. In other examples, the rings are between 1.0-0.5 times the balloon 20 length. More commonly the length of the rings 13 are between 2.5 and 1.5 times the balloon 20 diameter and typically between 1.5 and 0.5 times the balloon 20 diameter. Each ring 12, 13, 14 can be made from a different material so at to provide more than one advantage and function of the rings 12, 13, 14.

The rings 13 can be placed on the outer surface of the body of the balloon 20. In some examples, the rings 13 can be designed to retain the body of the strips 16 such that the position and orientation of the strips 16 are maintained. It can also be seen, that the strip 16 does not extend along the shoulders of the balloon. Thus, the strip can be elongated and can extend parallel with the axis of the balloon. FIG. 15A shows one strip 16 for simplicity, though it will be understood that 2, 3, 4, 5, or more strips could be used.

These rings 13 can be positioned over the expanded balloon 20 area and may have different properties than the rings 12, 14 on either end of the balloon 20. As illustrated in FIG. 15A, in some embodiments, the rings 13 positioned over the balloon 20 surface may be more elastic in property than those located on the ends of the balloon 20. This can allow the rings to accommodate the expansion and refolding of the balloon 20. In some examples, the rings used on the outer diameter of the balloon 20 are placed over the two ends of each separated strip. The strips 16 may also be glued, welded, restrained by friction fit, or otherwise attached to any of the rings described above.

In some embodiments, rows of strips and/or strip segments can be placed around the balloon 20. Some rows may extend over the entire length of the balloon 20 and other rows may not. In some examples, a row may include a plurality of strips in series that are separated by gaps. Placing strips in a series on the balloon can provide greater flexibility which can improve deliverability through tortuous anatomy.

As described previously, rings 12, 14, 13 can be used to retain the strip on the surface of the balloon 20. The rings can be connected to the strips in any number of different ways, as described in the various embodiments herein. In some embodiments, the ends of the strips 16 with no wedge dissectors can be used to attach to the rings. In other embodiments, the ends with wedge dissectors can attach to the rings.

Figure 15B:
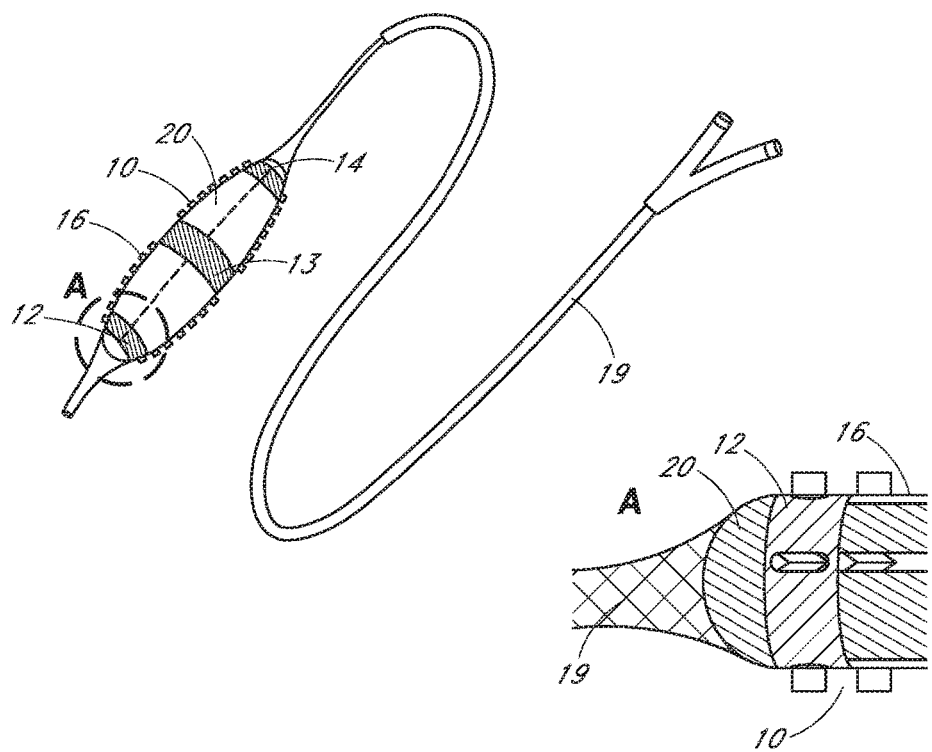
FIG. 15B is an angioplasty balloon with a cage having a plurality of segmented strips that are bound to the surface of the balloon by a plurality of rings.

FIG. 15B illustrates another embodiment of balloon catheter. A balloon 20 is shown with a cage 10 with four equally spaced rows of strips 16. Each row has two strips 16 that are laid in series. A ring 13 attaches the adjacent strips 16 to properly secure and orient the strips 16 across the surface of the balloon 20. Rings 12, 14 hold down the other ends of the strips.

The callout "A" provides an enlarged view of the distal end of the balloon 20 with cage 10. The hatching illustrated in callout "A" is provided to help visualize and delineate the different parts of the device. As shown, the end of the balloon 20 includes a ring 12 that secures a plurality of strips 16 to the surface of the balloon 20. The balloon 20 is disposed about a catheter 19. The ring 12 can be a heat shrink material. A wedge dissector is also shown extending through the ring. The placement of the strips is further clarified in FIG. 15C which shows how a pair of strips 16 which are laid in series such that the strips 16 span the length of the balloon 20.

Figure 15C:
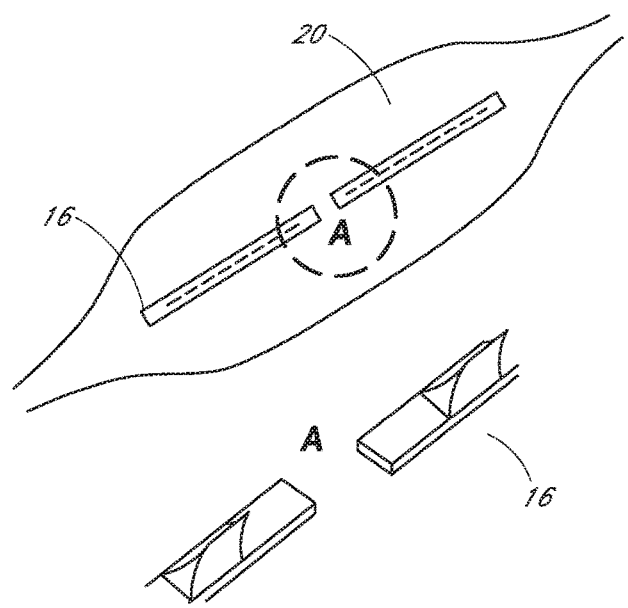
FIG. 15C shows an example of the placement of the segmented strips on the surface of the balloon.
Figure 15D:
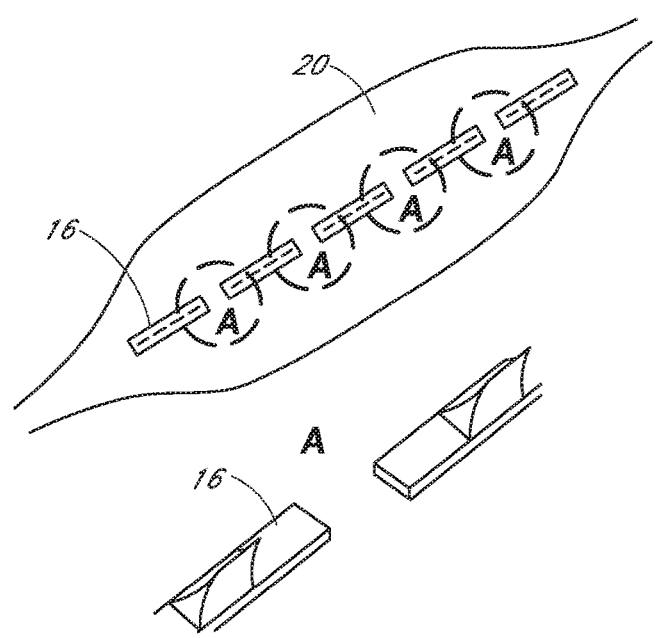
FIG. 15D is another example of the placement of a plurality of segmented strips onto the surface of an angioplasty balloon.
Figure 15E:
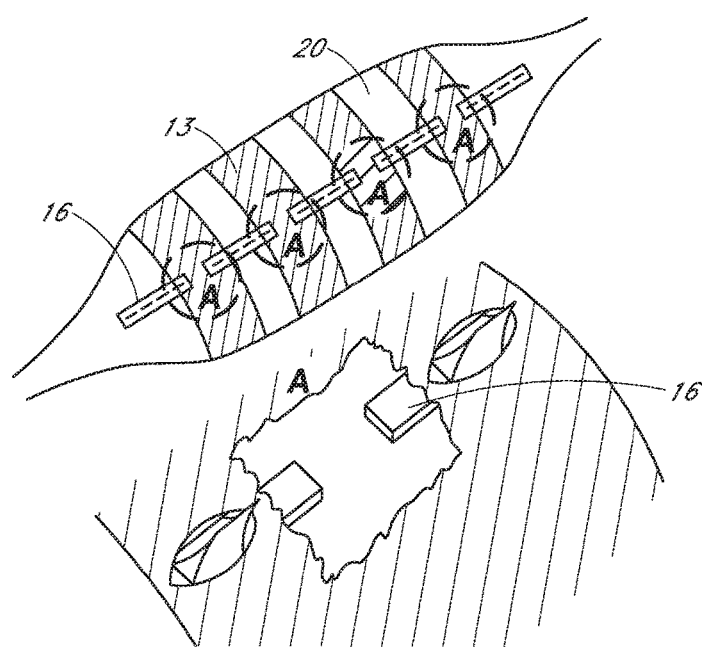
FIG. 15E illustrates an example of a plurality of segmented strips bound to the surface of a balloon by a plurality of rings.

To improve flexibility, the cage 10 can have rows that are made up of a greater number of strips 16 than illustrated in FIGS. 15B and 15C. FIGS. 15D-15E illustrate an example where five strips 16 are laid across the surface of the balloon 20 in series. As noted previously, each of these strips 16 can be secured on the surface of the balloon 20 by a plurality of rings 13. Callout "A" provides a cut away of the ring 13 to show the gap between the two strips 16 that are in series. As described above with reference to FIG. 14E, the wedge dissector can protrude through the ring 13 in a variety of ways. For example, the shape of the wedge dissector can cause the wedge dissector to poke through the material of the ring 13. As well, the ring 13 can have a plurality of holes cut into the rings 13 to allow the wedge dissectors to poke through.

In addition to having multiple strips in rows, the gap between the strips in a row can also be adjusted to increase flexibility. To ease manufacturing the linear alignment in the theta direction around the radius (angle drift) and the spacing alignment between the strips 16 (gap) can have a relatively broad tolerance creating greater options in developing the manufacturing process and choosing tools. In some cases, the gap tolerance can be ±5 mm and the angle drift ±25 degrees; ±3 mm and the angle drift ±10 degrees; and ±2 mm and the angle drift ±5 degrees. Cage designs that require greater tortuosity can utilize the periodic strip placements in a linear sequence with spaced apart strips. This can enable the balloon to manage bends and turns in anatomical spaces with less stress on the strips and more effective pushability of the entire system.

As shown herein many of the strips 16 have a flat bottom. This can help the strips 16 sit on the surface of the balloon and to maintain the orientation of the wedge dissectors. This can prevent rotational movement of the strips 16 on the surface of the balloon 20.

Three unique features that all strip and ring configurations can work to achieve are 1) perpendicularity of the wedge dissectors to the balloon surface, 2) maintaining flat and low profile of the strips on the balloon, aiding in limiting the wedge dissectors from damaging tissue on its journey, and 3) either assisting in deflation of the balloon or producing a minimal burden on the typical balloon deflation characteristics. To achieve these features strips typically have a flat bottom, are bounding to the balloon with rings on either end of the strip, are folded to limit wedge dissector interaction with tissue on its journey, and when a ring lays over the wedge dissectors the wedge dissectors poke through the rings and the majority of the wedge dissector height is still available for penetration into the vessel. Although some designs utilize rings to produce forces on the balloon enabling more effective balloon deflation by either pulling on the strips end to end or by applying radial compression, in most designs the rings can support the strips by limiting strip movement, aiding in wedge dissector orientation, and preventing the strips from separating from the balloon. Design features that contribute to these functional characteristics include: strips that have flat bottoms enabling stable orientation of the wedge dissectors but are thin enough to be laid down tangential to the balloon or contained in a fold of the balloon during folding, spacing between the wedge dissectors does not have a cutting edge enabling rings to lay in the spacing and support strip retention, and the ends of the strips can be thinnest with no wedge dissectors enabling greater surface area for rings to bond to the strip and enabling the strip to be most flexible at the edge of the balloon where forces are highest during catheter migration to and from site of deployment. It will be understood that other benefits and advantages can also be provided.

The rings 12, 13, 14 can be attached to the strips 16 in a variety of ways. FIGS. 16A-C shows examples of the rings 12, 13, 14 secured to the strips 16. FIG. 16A shows a material wrapped around the balloon to form rings 12, 13, 14 such that the material of the ring can be secured to more than one strip. In some examples, as illustrated in FIG. 16B, the ring 12, 13, 14 can be wrapped about a portion of each strip. This can be accomplished in the same way as illustrated in FIG. 10, where each of the rings can have an upper layer and bottom layer that wraps around a portion of the strip 16. FIG. 16C illustrates a solid ring 12, 13, 14 that can be attached to a portion of the balloon. A portion of the strip can be secured to the ring.

As discussed herein, many of the embodiments can use a heat shrink material for part of, or the entire ring 12, 13, 14. Heat shrink material generally starts from an extruded tube that is cross-linked using a form of radiation. The tube can be stretched or otherwise formed to the desired thickness. For example, it can be stretched to a flexible microscopically-thin-wall tubing, it can be made rigid from a heavy-wall tubing, or it can be somewhere in-between. Cross-linking can create a diameter memory and can be designed with a shrink ratio from 2:1 up to 10:1. Heat shrink typically shrinks only in the radial direction but can also shrink in length.

Heat shrink material can be manufactured from a thermoplastic material, such as polyolefin, fluoropolymer (including fluorinated ethylene-propylene (FEP), polytetrafluoroethylene (PTFE) or polyvinylidene fluoride (PVDF)(e.g. KYNAR)), polyvinyl chloride (PVC), neoprene, silicone, elastomer or synthetic rubber and fluoropolymer elastomer (e.g. VITON). When a flexible material is desired, such as one that expands with a balloon, the heat shrink material can include one or more of polyolefin, silicone, elastomer or VITON (synthetic rubber and fluoropolymer elastomer).

Heat shrink material in the form of a tube can be used to slide onto or over the strips 16. The tube can have a shrink ratio of 3:1 or higher (e.g. 3.5:1, 4:1, 4.5:1, 5:1, 6:1) and allow for gentle heat shrinking to prevent any balloon deformation or other changing of the balloon's properties. The material can be flexible enough to conform to the balloon through a range of balloon diameters (such as typical with semi-compliant balloon technology ~5 mm diameter range), and may have an adhesive or other coating to support the bonding of the heat shrink material and balloon. The heat shrink material can be a thin film. The heat shrink material may also be in the form of a sheet or multiple sheets instead of a tube.

A method of retrofitting a balloon catheter with a cage can include any of the following steps. Positioning strips around an inflated balloon. The strips may include wedge dissectors. The strips can be positioned equally spaced around the inflated balloon. The strips can extend primarily longitudinally. The strips may be positioned serially in rows, such as 2-6 rows, each with 2-6 strips. The strips can be attached either permanently or temporarily to the balloon with an adhesive. Heat shrink material can be positioned around the ends of the strips as a ring. Individual rings of heat shrink material can connect to or cover ends of multiple strips positioned circumferentially around the balloon. Individual rings of heat shrink material can also connect to or cover ends of adjacent strips positioned serially in a row. Heat can then be applied to shrink the heat shrink material. The balloon can be deflated and then sterilized in preparation for use.

Figure 17:
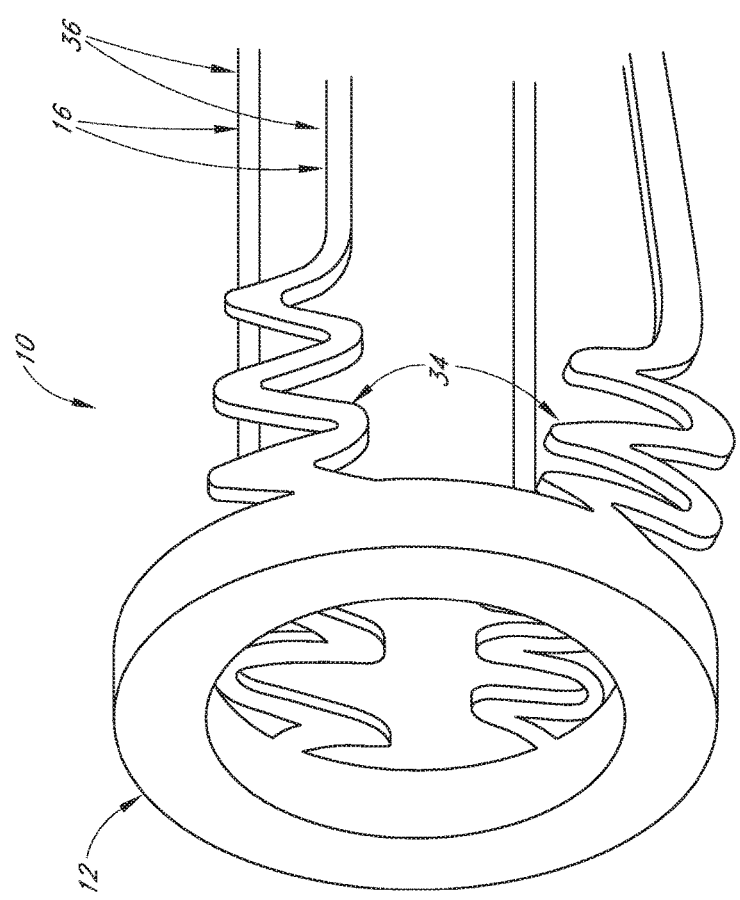
FIG. 17 illustrates a schematic view showing a detail of an embodiment of a cage with a spring.

Turning now to FIG. 17, a schematic view is illustrated showing a detail of a cage 10. In some embodiments, the strip 16 is shown having a section 34 composed of a spring zone. The spring section of the strip 16 can provide a plurality of benefits. For example, the spring section 34 can increase the flexibility of the cage 10. Increasing the flexibility of the cage 10 can allow the cage 10 to more easily pass through the tortuous geometry of a blood vessel. The spring section 34 can also provide a wider base for the wedge dissectors 26, to help the wedge dissectors 26 remain in the desired orientation.

In some embodiments, the spring section 34 can interface with a surface of the balloon 20. The spring section can help the strip 16 to remain in the correct position with the wedge dissectors 26 in an outwardly projecting orientation. In some examples, the spring section can counteract a sideways bending moment on the spike such that the wedge dissectors 26 do not bend, flex, or change position an undesirable amount. In some embodiments, the spring section 34 can also provide the benefit of assisting the balloon 20 in refolding post inflation. The spring can add mechanical tension on the balloon 20 to return it to a compressed state and further aid the rings in compressing the balloon 20 during deflation cycles.

Figure 18:
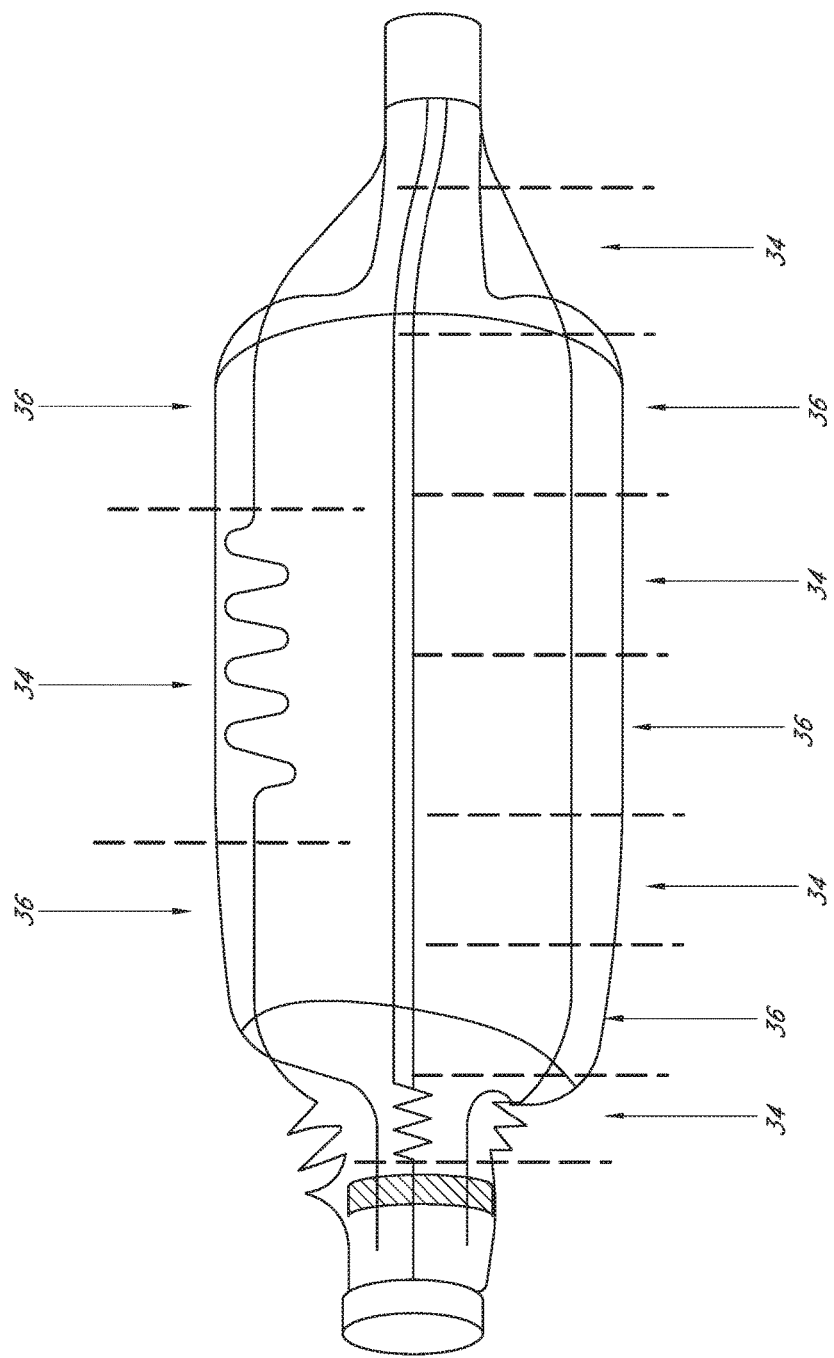
FIG. 18 illustrates various an embodiments of a cage utilizing aspects of the spring detail of FIG. 18.

The spring section 34 can have an undulating configuration and be connected to a straight section 36. In some examples, the wedge dissectors 26 can be located on the straight section. In other embodiments, the spring section can be sinusoidal. As illustrated in FIG. 18, the spring section is shown having a larger amplitude at the proximal end as compared to the distal end. The amplitude can decrease while the period increases along the spring section towards the straight section in a distal direction. In some embodiments, one side of the spring section can have a larger amplitude than the opposite side. In some embodiments, the spring section can be symmetrical.

Figure 19:
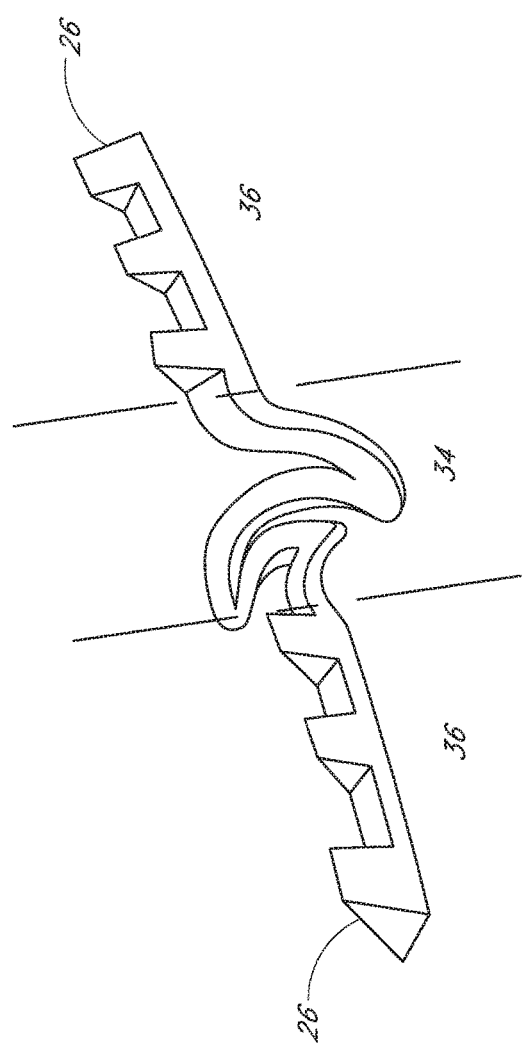
FIG. 19 shows a portion of a cage including a spring strip and spike configuration.

FIG. 18 illustrates various embodiments of the cage 10 utilizing the spring section 34 and straight section 36. Any number of different patterns can be used. FIG. 19 shows a detail of wedge dissectors 26 on straight sections 36.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

Similarly, this method of disclosure, is not to be interpreted as reflecting an intention that any claim require more features than are expressly recited in that claim. Rather, as the following claims reflect, inventive aspects lie in a combination of fewer than all features of any single foregoing disclosed embodiment. Thus, the claims following the Detailed Description are hereby expressly incorporated into this Detailed Description, with each claim standing on its own as a separate embodiment.

What is claimed is:

1. A balloon catheter comprising:
   an elongate member having an inner lumen, the elongate member defining a longitudinal axis;
   a balloon connected to the elongate member at a distal end of the elongate member;
   a cage for positioning about the balloon comprising:
      a plurality of strips, each strip of the plurality of strips including a plurality of wedge dissectors spaced apart along a surface of the strip by open spaces between adjacent wedge dissectors on the strip such that a height of the adjacent wedge dissectors is greater than a height of the open spaces in between adjacent wedge dissectors, each strip extending longitudinally along an outer surface of the balloon; and
      a plurality of rings configured to secure the plurality of strips to the balloon catheter, wherein each strip of the plurality of strips has a first ring of the plurality of rings at a distal end, a second ring of the plurality of rings at a proximal end, and at least a portion of the strip between the distal and proximal ends remaining uncovered by and/or unconnected to any ring, wherein at least some of the rings of the plurality of rings comprise a heat shrink material;
   wherein the balloon and cage are configured to have an initial state and an expanded state, the plurality of strips configured to move with the balloon as it moves toward the expanded state,
   wherein each ring of the plurality of rings comprise a central aperture and a plurality of holes offset from the central aperture and comprising a narrowed portion and a wider portion, wherein the wider portion is configured to accommodate each wedge dissector, and the narrowed portion is configured to accommodate each open space between wedge dissectors.

2. The balloon catheter of claim 1, wherein the heat shrink material comprises one or more of polyolefin, silicone, elastomer or synthetic rubber and fluoropolymer elastomer.

3. The balloon catheter of claim 1, wherein the plurality of rings secure the plurality of strips to distal and proximal ends of the balloon.

4. The balloon catheter of claim 1, wherein at least some of the strips of the plurality of strips are secured with rings at intermediate points of the balloon.

5. The balloon catheter of claim 1, wherein at least some of the strips of the plurality of strips extend longitudinally in a helical pattern across the balloon.

6. The balloon catheter of claim 1, wherein at least some of the strips of the plurality of strips extend parallel to the longitudinal axis across the balloon.

7. The balloon catheter of claim 1, wherein at least some of the rings of the plurality of rings comprise a part ring having a top layer of heat sink material and a bottom layer, an end of a strip of the plurality of strips sandwiched between the top layer and the bottom layer.

8. The balloon catheter of claim 1, wherein at least one end of each of the strips of the plurality of strips forms a hook, and wherein each hook is disposed about a portion of an end of the balloon.

9. The balloon catheter of claim 1, wherein a portion of each strip of the plurality of strips has a grooved surface where the strip contacts a ring of the plurality of rings.

10. The balloon catheter of claim 1, wherein each ring of the plurality of rings is free-floating about the balloon.

11. The balloon catheter of claim 1, wherein a portion of at least some of the strips of the plurality of strips includes a spring.

12. The balloon catheter of claim 1, wherein each of ring of the plurality of rings includes a groove that can accommodate a width of one of the strips of the plurality of strips.

13. The balloon catheter of claim 1, wherein the strips of the plurality of strips are positioned serially in rows around the balloon with 4 rows, each having between 2-6 strips per row.

14. The balloon catheter of claim 1, wherein a spacing length between the wedge dissectors is from 4:1 to 3:1 space to length.

15. The balloon catheter of claim 1, wherein a spacing length between the wedge dissectors is from 3:1 to 1:1 space to length.

16. The balloon catheter of claim 1, wherein a spacing length between the wedge dissectors is from 3:1 to 1:1 space to length.

17. A method of retrofitting a balloon catheter with a cage comprising:
   positioning a plurality of strips around an inflated balloon of a balloon catheter, the strips being positioned equally spaced around the inflated balloon, each strip of the plurality of strips including a plurality of wedge dissectors spaced apart along a surface of the strip by open spaces between adjacent wedge dissectors on the strip such that a height of the adjacent wedge dissectors is greater than a height of the open spaces in between adjacent wedge dissectors;
   advancing rings of heat shrink material over the balloon so that each end of the strips of the plurality of strips is covered by a ring heat shrink material; and
   heating the rings of heat shrink material to shrink the rings of heat shrink material to thereby secure the plurality of strips to the balloon, at least a portion of each strip of the plurality of strips between distal and proximal ends of the strip remaining uncovered by and/or unconnected to any ring of heat shrink material,
   wherein each of the rings comprise a central aperture and a plurality of holes offset from the central aperture and comprising a narrowed portion and a wider portion, wherein the wider portion is configured to accommodate each wedge dissector, and the narrowed portion is configured to accommodate each open space between wedge dissectors.

18. The method of claim 17, wherein positioning a plurality of strips around an inflated balloon further comprises positioning the strips to extend primarily longitudinally.

19. The method of claim 17, wherein positioning a plurality of strips around an inflated balloon further comprises positioning the strips serially in rows around the balloon with 4 rows, each having between 2-6 strips per row.

20. The method of claim 17, further comprising attaching the strips either permanently or temporarily to the balloon with an adhesive.

21. The method of claim 17, wherein advancing rings of heat shrink material over the balloon further comprises covering a distal end of distal-most strips of the plurality of strips with a single ring of heat shrink material.

22. The method of claim 21, wherein advancing rings of heat shrink material over the balloon further comprises covering a proximal end of proximal-most strips of the plurality of strips with a single ring of heat shrink material.

* * * * *